(12) United States Patent
Verenchikov et al.

(10) Patent No.: US 10,192,723 B2
(45) Date of Patent: Jan. 29, 2019

(54) SOFT IONIZATION BASED ON CONDITIONED GLOW DISCHARGE FOR QUANTITATIVE ANALYSIS

(71) Applicant: LECO Corporation, St. Joseph, MI (US)

(72) Inventors: Anatoly N. Verenchikov, St. Petersburg (RU); Alexander Kolosov, Bar (ME)

(73) Assignee: LECO Corporation, St. Joseph, MI (US)

( * ) Notice: Subject to any disclaimer, the term of this patent is extended or adjusted under 35 U.S.C. 154(b) by 0 days.

(21) Appl. No.: 15/508,800

(22) PCT Filed: Sep. 4, 2015

(86) PCT No.: PCT/US2015/048501
§ 371 (c)(1),
(2) Date: Mar. 3, 2017

(87) PCT Pub. No.: WO2016/037034
PCT Pub. Date: Mar. 10, 2016

(65) Prior Publication Data
US 2017/0278688 A1 Sep. 28, 2017

Related U.S. Application Data

(60) Provisional application No. 62/046,030, filed on Sep. 4, 2014.

(51) Int. Cl.
*H01J 49/00* (2006.01)
*H01J 49/10* (2006.01)
(Continued)

(52) U.S. Cl.
CPC ...... *H01J 49/0031* (2013.01); *H01J 49/0036* (2013.01); *H01J 49/0418* (2013.01);
(Continued)

(58) Field of Classification Search
None
See application file for complete search history.

(56) References Cited

U.S. PATENT DOCUMENTS 5,086,226 A    2/1992  Marcus
9,070,541 B2 *  6/2015  Verenchikov ......... H01J 49/107
(Continued)

FOREIGN PATENT DOCUMENTS

CN    1768411 A    5/2006
JP    2004171859 A    7/2010
(Continued)

OTHER PUBLICATIONS

Japanese Office Action for related Application No. 2017-507970 dated Mar. 1, 2018.
(Continued)

*Primary Examiner* — Andrew Smyth
(74) *Attorney, Agent, or Firm* — Honigman Miller Schwartz and Cohn LLP

(57) ABSTRACT

One aspect of the disclosure provides a method of mass spectrometric analysis that includes producing either glow discharge within a noble gas between 3-100 mBar pressure, sampling and conditioning glow discharge products within a gas flow through a conductive channel, removing charged particles while transferring excited Ridberg atoms, and mixing conditioned discharge products with analyte flow within an enclosed chamber at elevated temperatures above 150° Celsius for producing a Penning reaction between analyte molecules and Ridberg atoms. The method further includes sampling, by a gas flow, said analyte ions for mass spectrometric analysis, and at least one of the following steps: (i) removing charge within said conditioning channel; (ii) coaxially mixing of analyte flow with the flow of conditioned plasma; and (iii) cooling of the mixed flow within a sonic or supersonic jet for reducing the region of Penning ionization to cold jet.

16 Claims, 14 Drawing Sheets

(51) Int. Cl.
  *H01J 49/14* (2006.01)
  *H01J 49/04* (2006.01)
  *G01N 30/84* (2006.01)

(52) U.S. Cl.
  CPC .......... *H01J 49/102* (2013.01); *H01J 49/145* (2013.01); *G01N 2030/8482* (2013.01)

(56) References Cited

U.S. PATENT DOCUMENTS

| | | |
|---|---|---|
| 2010/0096542 A1 | 4/2010 | Whitehouse et al. |
| 2012/0056086 A1 | 3/2012 | Bandura et al. |
| 2012/0326022 A1* | 12/2012 | Kumano ............. H01J 49/0409 250/282 |
| 2013/0048851 A1 | 2/2013 | Kumano et al. |
| 2013/0140453 A1* | 6/2013 | Verenchikov ......... H01J 49/107 250/282 |

FOREIGN PATENT DOCUMENTS

| | | |
|---|---|---|
| JP | 2010157499 A | 7/2010 |
| JP | 2013541130 A | 11/2013 |

OTHER PUBLICATIONS

International Search Report dated Dec. 7, 2015, relating to International Application No. PCT/US2015/048501.

Chinese Office Action for the related Application No. 201580047322.4 dated Nov. 3, 2017.

\* cited by examiner

| Method | Soft | Uniform Ionization | Truly Quantitative, Linear, No Suppression | Range of Volatility | Identification Via Fragment Libraries |
|---|---|---|---|---|---|
| ESI, APCI | Yes | No | No | Both | No |
| MALDI | Yes | No | No | Non-vol | No |
| LC-APPI | Some | No | No | Both | No |
| EI | No | Yes | Yes | Semi-vol | Yes |
| CI | Some | No | No | Semi-vol | No |
| FI | Some | No | No | Both | No |
| Cold-EI | Some | Yes | Yes | Semi-vol | Some |
| GC-PI/PPI | Some | No | No | Semi-vol | No |
| GD direct | No | Some | Some | Semi-vol | No |
| GD chem | Some | No | No | Semi-vol | No |
| CGD | Yes | Yes | Yes | Semi-vol | Yes |

FIG. 14

SOFT IONIZATION BASED ON CONDITIONED GLOW DISCHARGE FOR QUANTITATIVE ANALYSIS

This Application is a national stage application of International Application No. PCT/US2015/048501 filed on Sep. 4, 2015, which claims the benefit of U.S. Provisional Application No. 62/046,030 filed on Sep. 4, 2014, which is entirely incorporated herein by reference. The entire contents of these applications are incorporated herein by reference in their entirety.

TECHNICAL FIELD

This disclosure relates to mass spectrometry. More specifically, this disclosure relates to mass spectrometry using a soft and quantitatively ionizing source based on conditioned glow discharge ionization.

BACKGROUND

Development of soft ionization methods, like Electrospray (ESI) and Matrix Assisted Laser Desorption/Ionization (MALDI) have extended the field of mass spectrometric analysis to wide class of labile compounds—such as peptides, nucleotides, proteins, and lipids—and have triggered the development of wide range of biological and medical applications. The methods are known to be limited to compounds which readily produce ions in liquid, such as ionic salts, and to polar compounds, readily producing protonated $MH^+$ and deprotonated ions $(M-H)^-$. The range of soft ionized compounds was extended to semi-polar compounds with introduction of Atmospheric Pressure Chemical Ionization (APCI) and Atmospheric Pressure Photo Ionization methods (APPI) methods. One shortcoming, however, is that these soft ionizing methods are not fully quantitative because the nature of the analyzed compounds define and vary both the ionization efficiency and the gas-phase stability against competitive ion molecular reactions.

On the other pole, the truly quantitative method of electron impact ionization (EI), wherein compound vapors are ionized by electron bombardment, has long existed. The ionization efficiency stays constant in wide range of analyte concentration, usually measured as sample load through a gas chromatograph (GC). Typically, linearity is sustained from a limit of detection (LOD) being as low as ten femtograms (10 fg) in most sensitive instruments and up to ten nanograms (10 ng) load range (i.e. at least within six orders of dynamic range). The ionization efficiency (i.e. response versus load) is mostly non-dependent on molecule nature, and stays independent on other coeluting compounds and matrix. This allows the EI method to be uniform across chemical classes and truly quantitative. The EI method, however, is limited to semi-volatile compounds, and it is not soft is not soft because it produces extensive fragmentation.

In addition to coupling with an EI method source, GC separation has been coupled to alternative and notably softer ionization methods—such as chemical ionization (CI) and field ionization (FI)—which provide more intensive molecular peak. The CI technique, however, is also prone to matrix and mutual interference effects. With this ionization method, both ionization efficiency and spectra content strongly depend on instrumental parameters. Thus, the CI technique is not considered to be fully soft, truly quantitative, or capable of providing library spectra. And the CI technique is also considered "dirty" due to the rapid contamination of the ion source. The FI method is frequently regarded as a soft ionization method; however, it is tricky, unstable, and insensitive with typical detection limit of only around one hundred picograms (100 pg). For this reason, the FI method has not been widely adopted.

Photo ionization (PI) and photo-chemical ionization (APPI) methods are much softer compared to EI, though still produces fragments for highly fragile compounds. Schlag describes in U.S. Pat. No. 4,570,066, which is fully incorporated herein by reference, that multi-photon ionization for laser desorbed nucleotides and short peptides, along with their cooling by a supersonic jet with subsequent multi-photon resonance ionization, which appeared to be moderately soft. The method was not widely adopted due to selective ionization, insufficient softness, and a limited class of analyzed compounds.

Glow discharge has been long employed in mass spectrometry for elemental and organic analysis, such as in F. W. Aston, MASS SPECTRA AND ISOTOPES, $2^{nd}$ edition, Longman Green, N.Y., 1942, which is fully incorporated herein by reference. In Hunt et. al, Anal. Chem vol. 47 (1975) 1730 (which is fully incorporated herein by reference), a Taundsen glow discharge was proposed for ionizing dopant gas in a CI source. U.S. Pat. No. 4,321,467 (which is fully incorporated herein by reference) proposes organics ionization in flow-afterglow at mbar-level gas pressures. VG Analytics introduced liquid samples via Thermospray interface and induced a glow discharge in the fore-vacuum region, as described in U.S. Pat. No. 4,647,772 and U.S. Pat. No. 4,794,252 (each of which is fully incorporated herein by reference). In U.S. Pat. No. 4,849,628 (which is fully incorporated herein by reference), McLuckey suggested sampling of liquid vapors from atmospheric pressure region into a glow discharge within a fore-vacuum stage at one to ten mbar gas pressure. Lubman et al. suggested ionized gaseous and liquid samples within Helium glow discharge at atmospheric pressure, as described in Applied Spectroscopy, 44 (1990) 1391 and Anal. Chem. 64 (1992) 1426 (each of which is fully incorporated herein by reference). Numerous groups have attempted to improve the softness and analytical merits of the glow discharge ionization sources. In spite of large variety of glow discharge sources, the employed ionization methods are split between two categories: (a) direct ionization and (b) chemical ionization.

Direct ionization in glow discharges occurs primarily due to Penning ionization by excited metastable of noble gases, while minor channels correspond to charge transfer from discharge ions and to electron impact ionization. Such ionization is likely to be quantitative, but harsh. As an example, Bertand et. al in JASMS, 5 (1994) 305 (which is fully incorporated herein by reference), exposed organic analytes to mBar glow discharge and demonstrated linear signal response within five orders of dynamic range, while obtaining spectra with softness varying from EI to CI spectra. Both sensitivity and softness appear strongly dependent on the analyzed compound and on the parameters of ion source. Adding dopant gases improves the intensity of molecular protonated ions and forms spectra similar to CI ones, as shown by Mason et al. in Int. J. Mass Spectrom. Ion Proc. 91 (1989) 209 (which is fully incorporated herein by reference).

The chemical ionization in glow discharges (or by sampled products of glow discharge) occurs primarily due to proton transfer from protonated water clusters, originating from ubiquitous water traces in technical purity gases. Proton transfer from water clusters has been intentionally promoted in a controlled proton transfer reaction (PTR) mass spectrometry as described by Hansel et al. in Int. J.

Mass Spectrom. Ion Proc. 149 (1995) 609 (which is fully incorporated herein by reference). Lubman et al. ionized gaseous and liquid samples within Helium glow discharge at atmospheric pressure, as described in Applied Spectroscopy, 44 (1990) 1391 and Anal. Chem. 64 (1992) 1426 (each of which is fully incorporated herein by reference). Adding water with liquid samples substantially improved softness of organic spectra. However, the proton transfer reactions caused non-linear signal per concentration response and non-uniform ionization. Efficiency of ionization varied within three orders of magnitude between analyzed compounds. Proton affinity is known to depend on compound polarity, which explains the non-uniform ionization between chemical classes. Operation at atmospheric (as compared to mbar) pressures increases the role of ion molecular reactions, which explains mutual analyte interferences and matrix suppression effects, even at large excess of the charging agent.

A DART glow discharge method has been described in Andrade et. al, Anal. Chem, 80 (2008) 2646-2653 (which is fully incorporated herein by reference), where volatile compounds are mixed with glow discharge in helium at atmospheric pressure. Though the method describes Penning ionization as the main mechanism, large number of gas collisions lead to significant distortions by ion molecular reactions. Thus, this also produces protonated ions for polar compounds and, hence, is also prone to discrimination and interference effects. Thus, glow discharge ionization is likely to be either (a) quantitative but harsh at direct GD ionization, or (b) soft but not quantitative at chemical ionization, primary implemented by proton transfer from water clusters.

In WO 2012/024570 (which is fully incorporated herein by reference), the inventors of this disclosure attempted to soften direct ionization in glow discharge by using a conditioner (i.e. a conductive tube for controlling plasma residence time prior to sampling discharge products into an ion-molecular reactor with analyte). GC inlet, purified gases, and clean materials were used to reduce the amount of quenching parasitic vapors. However, the conditioning appears strongly dependent on trace amount of vapors, strongly reduces efficiency of ionization, so the choice remained the same—either quantitative or soft.

SUMMARY

This disclosure provides the long waited combination of soft and quantitative ionization accomplished by a conditioned glow discharge method. The method also inducing effective identification using a U.S. National Institute of Standards and Technology (NIST) library search. This method accomplishes such a desirable ionization by: (a) generating large fluxes of metastable noble gas atoms at mBar glow discharge; (b) sampling those metastable particles and suppressing charged particles; and (c) using gaseous cooling for analyte molecules simultaneously with Penning ionization in cold supersonic gas jet at limited number of gas collisions.

One astonishing aspect of the method provided by this disclosure is the effect of the gaseous cooling on the analyte ion stabilization. Cooling of analyte and of surrounding Argon gas dramatically reduces the amount of fragments and provides spectra with molecular M+ ions only. In an implementation, the supersonic jet cooling is arranged at coaxial sampling of analyte molecules and of the glow discharge products.

Gaseous cooling to overweighs the excitation effects at glow discharge formation of metastable atoms, and soft ionization occurs at a wide range of discharge parameters. This allows reaching large fluxes of metastable atoms, while using very moderate conditioning for removal of charged particles. As a result, the efficiency of ionization approaches unity (ratio of formed ions per injected analyte molecule) and appears uniform between chemical classes of analytes.

Efficient ionization by the method is reached within a supersonic jet with small number of neutral collisions, which is estimated to about 100. Thus, even at reasonable technical purity of gases and materials, the source strongly reduces the amount of cluster formation and of other parasitic ion molecular reactions with analyte ions.

The novel method presented by this disclosure is a conditioned glow discharge ionization method that called Cold GD. Experimental tests of this novel Cold GD method have confirmed:

1.) Soft ionization for labile molecules—such as alkanes, phthalates, nitroses, and fatty acids—that are known to form intensive fragmentation in methods like EI, CI, Cold EI, and PI;

2.) Formation of molecular M+ ions only, which simplifies spectra identification, unlike prior art glow discharge and PI sources which form both M+ and MH+ ions;

3.) Uniform response between wide range of classes, confirmed for alkanes, PAH, PCB, phthalates, and nitro-containing compounds;

4.) Linear response within at least four orders of dynamic range, between one picogram (1 pg) and ten nanogram (10 ng) load via GC column;

5.) Absence of chemical discrimination, interference, and matrix effects at chemical matrix fluxes under 10 ng/sec;

6.) Ability to form NIST type of fragments at ion excitation within the ion transfer interface, which is characteristic for M+ ions and is useful for compound identification based on library spectra; and 7.) Fast response of the ion source, matching the speed of GC×GC analysis.

The combination of softness, true quantification, large dynamic range, and fast response opens numerous opportunities for improved analytical methods in the field of petroleomics and metabolimcs, so as utilizing multidimensional separations, like GC×GC-MS, GC-IMS-MS, GC-MS-MS for complex mixtures analysis. Some implementations and their novel aspects for quantitative analysis of complex mixtures and detection of ultratraces are described in this disclosure.

One aspect of the disclosure provides a method of mass spectrometric analysis including producing either RF or DC glow discharge within a noble gas at gas pressure between 3 and 100 mBar, sampling and conditioning glow discharge products within a gas flow through a conductive channel for removing charged particles while transferring excited Ridberg atoms, mixing conditioned discharge products with analyte flow within an enclosed chamber at elevated temperatures above 150° Celsius for producing a Penning reaction between the analyte molecules and the Ridberg atoms to generate ions of the analyte, and sampling the analyte ions (by a gas flow) for mass spectrometric analysis. The method also includes at least one of the following steps: (1) removing charge within the conditioning channel caused by charging of an insulating surface protruding through the conditioning channel; (2) coaxially mixing of analyte flow with the flow of conditioned plasma; and (3) cooling of the mixed flow within a sonic or supersonic jet for reducing the region of Penning ionization to cold jet.

Implementations of the disclosure may include one or more of the following optional features. In some implementations, the molecular ions of analyte are partially fragmented either at an ionization event or at a step of controllable collisional induced dissociation, and obtained fragment spectra are compared with library spectra of electron impact for analyte identification and for a structure elucidation. In some examples, the method further includes introducing less volatile compounds within a liquid or solid matrix to extend the range of analyte volatility whereat a matrix flux remains under 10 ng/sec and where the analyte sample is brought to a gas phase bone one of the following steps: (a) applying a rapid thermo desorption; (b) applying pulsed laser desorption; (c) applying nebulization a liquid sample with removal of solvent vapors by side or counter gas while passing through aerosol; and (d) applying nebulization at a flow rate under 10 nL/min pas capillary electrophoresis or nano liquid chromatography. The method may further include a step of upstream tandem chromatographic separation of the list comprising: (i) GC×GC; (ii) LC-GC; (iii) LC-LC; (iv) LC-CE.

In some implementations, for the purpose of enhanced selectivity at analysis of complex mixtures, the method further includes a step of mass or ion mobility selection of parent ions prior to the step of ion fragmentation. The method may further include a step of varying fragmentation energy. In some examples, for the purpose of enhanced analysis selectivity, the method further includes a step of adding a reagent gas into the region of conditioned glow discharge, thus converting Ridberg ions into reagent ions. In some implementations, the method further includes a step of mass-spectrometric analysis of the ionized analyte ions with a high resolution multi-reflecting time-of-flight mass spectrometer, operating in the regime of frequent encoded pulsing.

Another aspect of the disclosure provides a method of mass spectrometric analysis including quantitative and soft ionizing in a conditioned glow discharge ion source, alternated in time measuring of molecular mass and fragmentation of molecular ions, and compound identifying by comparing with library of electron impact spectra. This aspect of the disclosure may include one or more of the following optional features. In some examples, the method further includes at least one step of the group: (i) an upfront multi-stage chromatographic separation of analyte molecules; (ii) an upfront mass separation of molecular ions; (iii) ion mobility separation of molecular ions.

Yet another aspect of the disclosure provides a method for assembling an ion source for a mass spectrometry apparatus that includes providing a reactor chamber, arranging a glow discharge chamber adjacent to the reactor chamber, providing a tubular electrode extruding into an interior of the glow discharge chamber, arranging a sampling nozzle at an outlet end of the reactor chamber, providing a capillary for sample introduction, and arranging a mechanical fluid pump in a location to allow evacuation of gas. The mechanical fluid pump evacuates the gas from the glow discharge chamber past the sampling nozzle. The reactor chamber defines a sampling conditioning channel. The capillary passes through the glow discharge chamber, protrudes through the tubular electrode, and at least partially passes through the reactor chamber.

This aspect of the disclosure may include one or more of the following optional features. In some implementations, the method further includes charging an insulated surface that protrudes through the sampling conditioning channel. In some examples, the gas evacuated by the mechanical fluid pump is a noble gas, and the noble gas is pressurized within the glow discharge chamber prior to evacuation.

A fourth aspect of the disclosure provides an ion source for a mass spectrometry apparatus that includes a reactor chamber that defines a sampling conditioning channel, a glow discharge chamber residing adjacent to the reactor chamber, a tubular electrode that receives a voltage and extrudes into an interior of the glow discharge chamber, a sample nozzle residing at an outlet end of the reactor chamber, a capillary for sample introduction, and a mechanical fluid pump. The capillary passes through the glow discharge chamber, protrudes through the tubular electrode, and at least partially passes through the reactor chamber. The mechanical fluid pump resides in a location to allow evacuation of gas, and the mechanical fluid pump evacuates the gas from the glow discharge chamber past the sampling nozzle.

This aspect of the disclosure may include one or more of the following optional features. In some examples, the ion source further includes an insulated surface that protrudes through the sampling conditioning channel. In some implementations, the gas evacuated by the mechanical fluid pump is a noble gas, and the noble gas is pressurized within the glow discharge chamber prior to evacuation.

Yet another aspect of the disclosure provides an analytical method that includes quantitatively soft ionizing an analyte in a conditioned glow discharge ion source, alternating-in-time measuring of molecular mass and fragmentation of molecular ions, and identifying compounds by comparing with a library of electron impact spectra.

This aspect of the disclosure may include one or more of the following optional features. In some implementations, the ionizing step includes producing a glow discharge from a noble gas at an elevated pressure between 3-100 mBar, conditioning the glow discharge through a sampling conditioning channel, and ionizing an analyte by mixing the analyte with the conditioned glow discharge at an elevated temperature. In some examples, an insulated surface within the sampling conditioning channel is charged to remove charge of a flow through the sampling conditioning channel. The step of ionizing an analyte may include a coaxial mixing of a flow of the analyte with a flow of the glow discharge. In some examples, a step of cooling the ionized analyte within a jet occurs after the step of ionizing an analyte. In some implementations, the step of ionizing an analyte occurs at the throttle of a sampling nozzle.

Yet another aspect of the disclosure provides a method of conditioned glow discharge ionization including arranging an enclosed ionization chamber for minimal outgassing, heating the ionization chamber to an elevated temperature above 250 degrees Celsius, feeding a noble gas into the ionization chamber at a flow rate between one hundred milliliters per minute and one thousand milliliters per minute, evacuating the gas through a sampling conditioning channel, inducing glow discharge between a tubular electrode and a counter-electrode, inserting an insulating surface through the tubular electrode to stabilize the glow discharge inducement, creating a gas flow through the sampling conditioning channel to move the induced glow discharge products, protruding the insulating surface through the sampling conditioning channel, introducing an analyte sample, mixing the analyte sample with the glow discharge products in close vicinity or within a throttle of a sampling aperture, providing local cooling of the analyte sample within a gas cooling jet, wherein the gas cooling jet is formed within the sampling aperture, and directing products to a mass spectrometer.

This aspect of the disclosure includes may include the following optional feature. The insulating surface may be a quartz capillary, and the quartz capillary may introduce the analyzed sample.

DESCRIPTION OF DRAWINGS

FIG. 14 shows a table comparing characteristic of various ionization methods to characteristics of the CGD method accomplished by the apparatuses of FIGS. 5A-5B.

Like reference symbols in the various drawings indicate like elements.

DETAILED DESCRIPTION

Figure 5A:
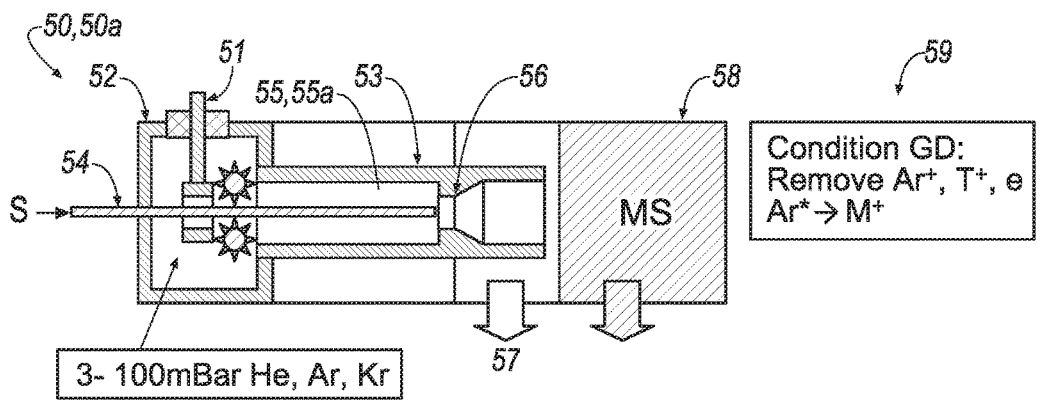
FIGS. 5A-5B are schematic views of example apparatuses for applying a Conditioned Gas Discharge (CGD) method for mass spectrometric analysis of complex mixtures of semi-volatile compounds.
Figure 5B:
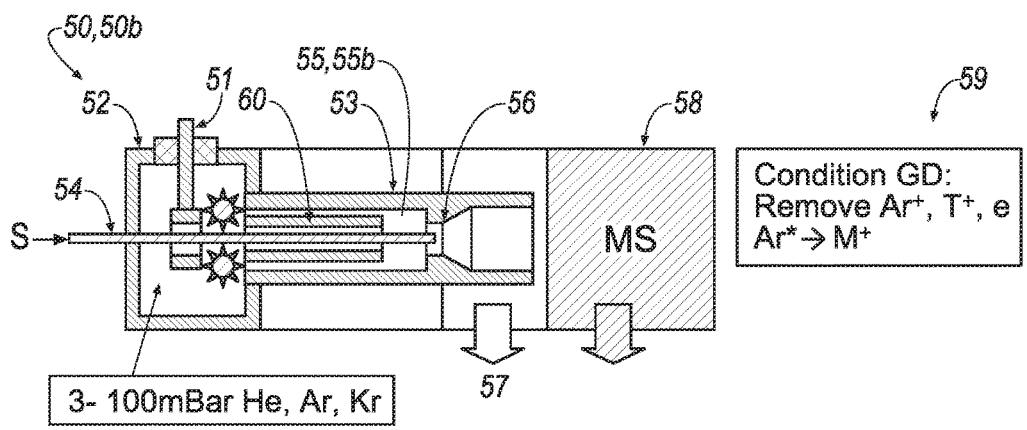

This disclosure describes methods and apparatuses for mass spectrometry utilizing a soft and quantitatively ionizing source based upon glow discharge ionization. Referring first to FIGS. 5A-5B, a conditioned glow discharge ionization mass spectrometry apparatus 50 and an accompanying conditioned glow discharge ("CGD") method, which are described in more detail hereinafter, are disclosed. Turning to FIG. 14, a review of the merits of various ionization methods is presented. The CGD method (summarized in row 1411)—which may be accomplished, for example, by utilization of apparatus 50—is compared with other ionization methods (summarized in rows 1401-1410). FIG. 14 indicates that some methods do provide ionization with particular characteristics (indicated by 'Yes'). other methods do not provide ionization with such characteristics (indicated by 'No'), and some method provide a limited ability of a certain characteristic (indicated by 'Some').

While soft ionizing methods such as ESI and MALDI (along with APCI and APPI), refer to rows 1401-1403, have extended the range of compounds that may be analyzed with mass spectrometry, these soft ionizing methods cannot be considered fully quantitative since the nature of the analyzed compounds define and vary both the ionization efficiency and the gas phase stability against competitive ion molecular reactions. A full quantitative analysis could be possible by accounting for variable efficiency of ionization; however, the ionization efficiency appears dependent on ion source parameters, on the analyzed solution, on mutual analyte interference, and on matrix effects. Signal changes nonlinear with analyte concentration and depends on concentration of coeluting compounds and chemical matrix. In the attempt of obtaining quantitative data, one should introduce an internal standard (preferably isotopic labeled) for each class of analyte and, preferably, for each analyzed compound. Accounting for the wide range of known labile compounds, which exceeds 50 million records in the Chemical Abstract Database, the internal standard approach appears unpractical for routine use of these soft ionization methods, except for particularly important analyses cases. Thus, widely used soft ionizing methods—ESI, MALDI, APCI and APPI—cannot be considered truly quantitative, as documented in FIG. 14.

Contrary to widely represented opinion, this disclosure claims that those soft ionization methods do not provide library spectra identification based on fragment spectra produced in tandem mass spectrometers (see right column in FIG. 14). Although peptides could be identified based on a library search, the spectra are not reproducible between instruments with strong variations of relative fragment intensities. Although fragment spectra for other compound classes could be interpreted, confident assignment between functional isomers belonging to different chemical classes would only be accomplished in rare circumstances. This looks to be the fundamental property of protonated ions.

Electron impact ionization (EI), refer to row 1404, is another ionization method. As illustrated in FIG. 14, this method is truly quantitative, but it is not soft; it produces extensive fragmentation. While it is not a soft method, the fragmentation produced by the EI method has been utilized as a benefit of the overall analytical method. Electron energy is kept at 70 eV in order to obtain standard fragment spectra, which is highly reproducible between various instruments. Gas chromatography (GC) is employed to separate analytes in time, so that individual fragment spectra could be deconvoluted (i.e. extracted based on fragments' simultaneous appearance in time). Extracted EI spectra are then submitted for comparison with a library of standard EI spectra for compound identification (see right column of FIG. 14). The method allows identification of several hundreds of compounds per single gas chromatograph-mass spectrometer (GC-MS) run. Two-dimensional gas chromatography (GC×GC) extends the limit to thousands of analyzed compounds per single run. However, the utilization of a GC-MS system with an EI ionization source chokes when sample complexity exceeds tens of thousands and individual fragment spectra, which can no longer be separated. Harshness of the EI method also limits the analysis to labile analyte molecules. For a wide range of particularly fragile (though semi-volatile) analytes, like alkanes, phthalates, nitroses, and many other classes, the EI spectra do not provide sufficient molecular peak intensity which affects the identification. In this case, an entire molecule of an analyte can be confused with its own subset. To this end, GC-MS applications have been longing for a complementary soft ionization technique.

The chemical ionization (CI) method, refer to row 1405, is not truly quantitative, and despite being softer than the EI method has only limited abilities to provide a soft ionization; it is not a truly soft method. And the CI method does not provide for library spectra. The field ionization (FI) method, refer to row 1406, also has only a limited ability to provide soft ionization. And it has not been widely adopted due to its instability and unfavorable detection limit.

The softness of the EI method has been improved with analyte cooling with a gas jet, as described by Amirav in U.S. Pat. No. 5,055,677, which is fully incorporated herein by reference. However, this improved EI method, refer to row 1407, does not provide truly soft ionization, but rather provides a reduction of fragment intensity and moderate enhancement of molecular ion intensity. And another shortcoming of this cold EI method is that the degree of fragmentation varies with experimental parameters.

The photo ionization (PI) method and related methods (such as APPI), refer to row 1408, are softer than the EI method, but still produce fragments when ionizing fragile compounds. Thus, while possessing a limited ability to produce soft ionization, it has a limited associated range and is not truly quantitative. With the use of sealed UV lamps these methods becomes suitable for wide range of moderately polar compounds. The PI method has been utilized for detection after GC, as described in U.S. Pat. No. 4,377,749, U.S. Pat. No. 4,413,185, and U.S. Pat. No. 4,398,152, each of which is fully incorporated herein by reference. In SU1159412 (fully incorporated herein by reference) and multiple scientific papers Revelsky et al. suggested using the PI method at atmospheric conditions for GC-MS analysis. Photo ionization is accompanied by damping of internal energy at atmospheric pressure which makes it much softer compared to vacuum UV ionization. To enhance efficiency of ionization there are added dopant vapors of acetone or benzene; thus promoting the formation of molecular $M^+$ and protonated $MH^+$ ions with little amount of fragmentation and with detection limit between one to ten picograms (1-10 pg). Some variations of the method are suggested in U.S. Pat. No. 5,541,519 and U.S. Pat. No. 5,338,931, each of which is fully incorporated herein by reference. However, the method may cause confusion in spectra interpretation with formation of either $M^+$ or $MH^+$ ions. Present experimentation shows that the method forms ionic clusters and moderate amount of fragment ions. Besides, the APPI method fails at analysis of saturated hydrocarbons (SHC) and does not ionize compounds with high ionization potential (PI) above 9-11 eV, like small mass halogenated compounds. The ionization efficiency depends on competition for proton with dopant, and there is a much higher spread of compound dependent ionization efficiency in the PI method compared to the EI method. Ionization efficiency varies with dopant concentration and is prone to chemical interference and suppression mechanisms. Thus, PI cannot be considered as a truly quantitative method. Same is even more related to LC-APPI sources, where competition for charge is inevitable at presence of large amount of solvents.

Glow discharge ionization, refer to rows 1409-1410, are generally split into direct glow discharge ionization (refer to row 1409) and chemical glow discharge ionization (refer to row 1410). Direct glow discharge ionization methods may be fully quantitative, but fail to achieve a soft ionization. Chemical glow discharge ionization methods may achieve soft ionization, but fail to by fully quantitative. WO 2012/024570, which is fully incorporated herein by reference, presents some advances, but ultimately fails to achieve both quantitative and soft ionization.

As a summary of FIG. 14, soft ionization methods, based on proton transfer, like ESI, MALDI, APCI and APPI, are widely adopted for providing molecular mass information. However, they are not uniform in ionization, not truly quantitative, are only applicable to a limited class of analyte compounds, and do not form library fragment spectra. In contrast, the electron impact (EI) ionization method is truly quantitative, provides uniform ionization, and forms library fragment spectra. However, it is not soft, which presents problems for identifying labile molecules and limits the sample complexity, since rich spectra have to be deconvoluted in GC-MS analysis. Complementary to EI methods—such as CI, cold EI, and FI—improve softness but present their own practical problems. Photoionization method with sealed UV lamp and dopant assisted chemical ionization are significantly softer, but are not uniform in ionization efficiency and are prone to interference effects, typical for methods with protonated molecular ions. Glow discharge methods can be as robust as the EI method; however, in past implementations there was always a compromise between softness and quantification features. One can chose between softness and quantification, but could not achieve both. Hence, the CGD method of row 1411 of FIG. 14 represents a novel ionization method with advantageous effects not presented in any other single ionization method of rows 1401-1410.

Attempts have been made to improve upon the ionization methods of rows 1401-1410, such as by utilizing a gas dampening or a gas jet cooling process. A gas dampening of these ionization methods may have direct effects on the softening of the ionization. For example, SU1159412 (which is fully incorporated herein by reference) proposes to use an atmospheric pressure dampening for softening of the photo ionization method. U.S. Pat. No. 6,504,150 (which is fully incorporated herein by reference) proposes gaseous dampening of MALDI generated ions. Lubman et. al has demonstrate much softer GD spectra at atmospheric pressure in Applied Spectroscopy, 44 (1990) 1391 and Anal. Chem. 64 (1992) 1426 (each of which is fully incorporated herein by reference). However, the operation at elevated gas pressures inevitably promotes chemical ionization at presence of technical clean gases (typical impurities above 1E-6) and source materials, which in turn causes formation of protonated ions by a non-quantitative ionization, resulting in non-uniform response between chemical classes.

Also, expanding upon the above-discussed gas jet cooling (see also row 1407), earlier publications suggest that prior collisional cooling of analyte molecules in supersonic jets have a positive effect on ion stability at subsequent "harsh" ionization at much lower gas pressures. U.S. Pat. No. 4,570,066 explores this technique for multi-photon ionization, and U.S. Pat. No. 5,055,677 explores this technique for EI ionization. Both of these references are fully incorporated herein by reference. Despite such a positive effect in some of the other methods, jet cooling appears insufficient at direct glow discharge ionization in glow discharge, as described and explained by McLuckey et. al, Anal. Chem, 60 (1988) 2220 (which is fully incorporated herein by reference). Cooling by gas jet means stabilizes molecules at charge transfer; however, this has not mitigated ion fragmentation during direct glow discharge ionization methods. Thus, utilization of either gas dampening or jet cooling has not resulted in soft and quantitative glow discharge ionization. As such attempts have failed to remedy the shortcoming illustrated in rows 1409-1410, ionization methods that combine softness with quantification are needed to improve the art of ionization for spectrometry.

Figure 1:
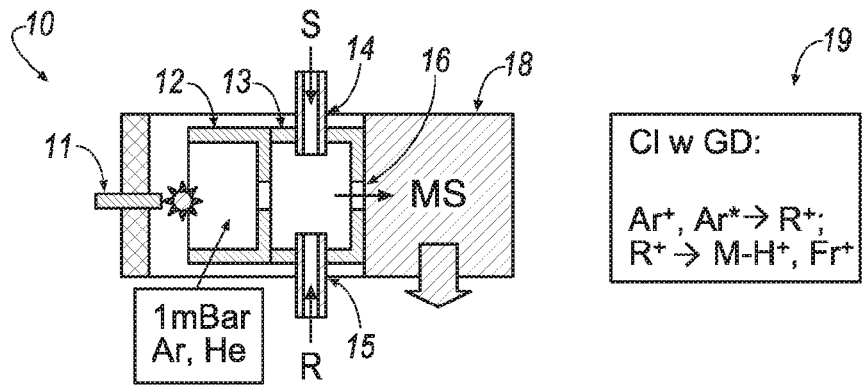
FIGS. 1-3 are schematic views of example chemical glow discharge ionization apparatuses.
Figure 2:
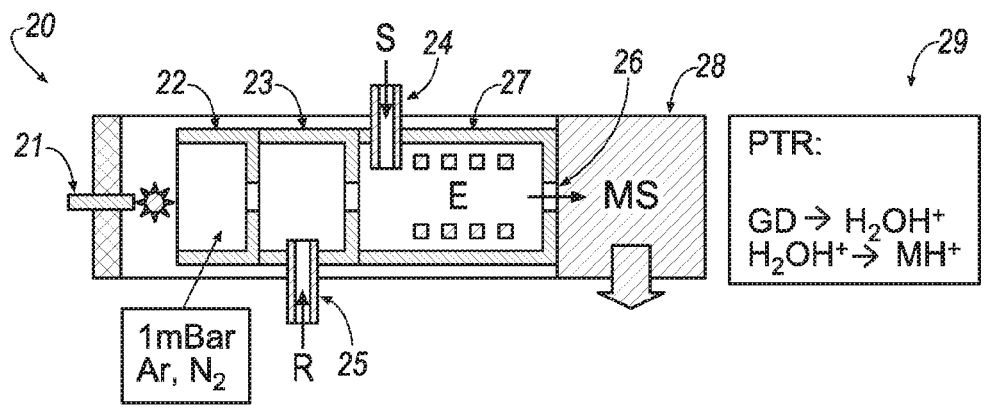
Figure 3:
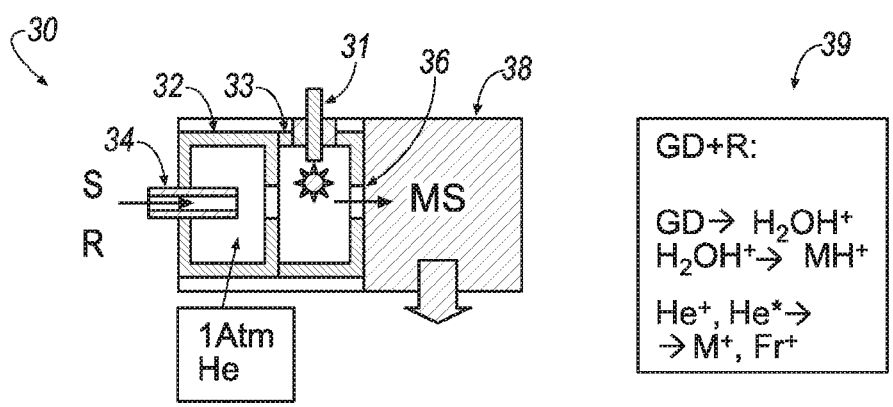

Chemical glow discharge ionization methods may utilize various implementations of apparatuses to achieve ionization for spectrometry analysis. Referring to FIGS. 1-3, schematic views of chemical glow discharge ionization apparatuses 10, 20, 30 are presented. Chemical ionization induced by glow discharge, including the steps of ionizing a reagent by glow discharge followed by a charge or proton transfer from those reagent ions to vapors of analyte, is utilized by the apparatuses 10, 20, 30 of FIGS. 1-3.

Referring specifically to FIG. 1, the chemical glow discharge ionization apparatus 10 employs glow discharge between electrodes 11 and 12 at about 1 mBar gas pressure of noble gases—such as Argon or Helium. The discharge forms ions and metastable particles $Ar^+$ and $Ar^*$, which are sampled into reaction chamber 13. Reagent vapors, typical for the CI method, are introduced into the reaction chamber 13 through line 15 at a much larger concentration than the analyte vapors, which are introduced into the reaction chamber 13 through line 14. Reagent ions are primarily formed by Penning ionization ($Ar^*+R\rightarrow Ar+R^+$). In turn, reagent ions transfer charge to analyte vapors and produce analyte ions, typically $M-H^+$ and their fragments $Fr^+$ ($R^+\rightarrow M-H^+$, $Fr^+$) with spectra very similar to CI for analysis by mass spectrometer 18. The method, which is summarized in icon 19, has been developed to avoid degradation of electron emitters in CI. Hunt, et al., *Positive and Negative Chemical Ionization Mass Spectrometry Using a Townsend Discharge Ion Source*, ANAL. CHEM., vol. 47, pg. 1730 (September 1975), incorporated fully herein by reference, provides additional information regarding a similar method to that which is carried out by apparatus 10.

Referring specifically to FIG. 2, the chemical glow discharge ionization apparatus 20 induces glow discharge in the chamber 22, aided by electrode 21, to produce large currents of ionizing particles. Water vapors are intentionally introduced, through reagent line 25, into a drift chamber 23, thus promoting formation of water clusters and arranging proton transfer reaction (PTR) to analyte vapors in reactor chamber 27. The reactor 27 employs a medium-strength electrostatic field E pressurized to an mBar pressure range to improve ion transfer within an elongated reactor for breaking larger water clusters $W_nH^+$ to $WH^+$. Thus, the reactor 27 reduces proton affinity of the reagent ion, and this way enhances ionization of analytes, which are introduced into the reactor chamber 27 through analyte line 24, with moderate proton affinity in the processes $WH^+\rightarrow MH^+$. The ionized analytes may be analyzed in mass spectrometer 28. The method, which is summarized in icon 29, has been developed for detection of ultra-traces in air and for breath analysis. Hansel, et al., *Proton Transfer Reaction Mass Spectrometry*, INT'L J. MASS SPECTROM. & ION PROC., vol. 149, pg. 609 (1995), which is fully incorporated herein by reference, provides additional information regarding a similar method to that which is carried out by apparatus 20.

Referring specifically to FIG. 3, the chemical glow discharge ionization apparatus 30 employs liquid nebulization and evaporation within chamber 32, which receives sample S through analyte line 34. The chamber 32 samples analyte vapors and solvent into a glow discharge chamber 33 containing Helium at atmospheric pressure. Water traces in the gas act as a reagent to form water cluster ions, thus promoting soft ionization of analyte at RH+→MH+ processes within the chamber 33 and aided by electrode 31. The ionized sample is introduced into mass spectrometer 38 through a differentially-pumped orifice 36. Adding water solvent with liquid samples substantially improves softness for organic spectra. Lubman, et al., *Liquid Sample Injection Using an Atmospheric Pressure Direct Current Glow Discharge Ionization Source*, ANAL. CHEM., vol. 64, pg. 1426 (1992), which is fully incorporated herein by reference, provides additional information regarding a similar method to the method that is carried out by apparatus 30, which is summarized in icon 39. Exposure of analyte vapors to glow discharge also causes some moderate fragmentation. The proton transfer reactions caused non-linear signal per concentration response, resulting in non-uniform ionization. Efficiency of ionization of the method carried out by apparatus 30 can vary within three orders of magnitude between analyzed compounds.

Proton affinity depends on compound polarity, which explains the non-uniform ionization between chemical classes. Operation at atmospheric, rather than operating at mbar pressures, increases the role of ion molecular reactions, which explains mutual analyte interferences and matrix suppression effects, even at large excess of the charging agent. Thus, methods of chemical ionization induced by glow discharge in apparatuses 10, 20, 30 are relatively soft (though not being as soft as ESI or APCI which do not expose analyte to glow discharge), but is not truly quantitative.

Figure 4:
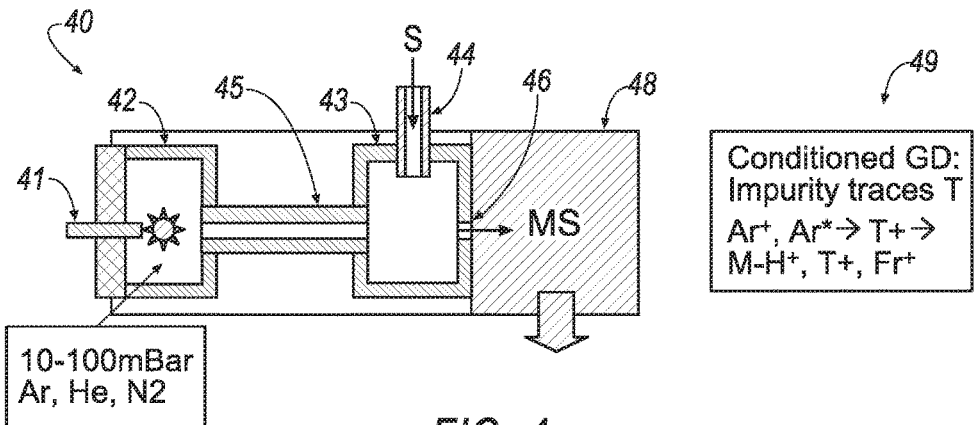
FIG. 4 is a schematic view of an example conditioned glow discharge ionization apparatus.

Referring to FIG. 4, a conditioned glow discharge ionization apparatus 40 employs a capillary 45 for conditioning glow discharge plasma between glow discharge chamber 42 and reactor chamber 43. A fine (e.g., 1.5-2 mm diameter) and sufficiently long (e.g., 10-20 mm) capillary 45: (a) screen the reactor chamber 43 from the strong electric field, (b) chill the sampled gas, and (c) remove at least fast electrons to leave ions and metastable discharge ions that produce analyte ions from sample injected through an orthogonal-set sample transfer line 44 and mixed with conditioned glow discharge products in the reactor chamber 43, which is typically 5-10 mm in diameter and length. The products are sampled into a mass spectrometer 48 via an aperture 46, which is usually sized with a 0.5-2 mm diameter. WO 2012/024570 by the present inventors, which is fully incorporated herein by reference, provides additional information regarding a similar method to the method that is carried out by apparatus 40, which is summarized in icon 49.

The method of FIG. 4 appears very sensitive to minor (at ppm level) impurities or traces in the auxiliary gas, to minor seal leaks, and to impurities in the source materials. This also makes the method sensitive to glow discharge regimes (arc versus glow discharge). As a result, so-called quenching of plasma components by chemical impurities defines both sensitivity and softness of the method, which makes it inconvenient for routine use.

In contrast to the ionization methods accomplished by apparatuses 10, 20, 30, 40, implementations of the present disclosure are directed toward providing a soft and quantitative ionization method, which may be referred to as a Cold Conditioned Glow Discharge method. Turning to FIGS. 5A-5B, schematic views of example conditioned glow discharge ionization mass spectrometry apparatuses 50 are illustrated for implementing mass spectrometric analysis of complex mixtures of semi-volatile compounds utilizing the ionization method of the present disclosure. The apparatus 50 includes a coaxial discharge tubular electrode 51, a glow discharge chamber 52, a reactor chamber 53 housing a sampling conditioning channel 55, a sampling nozzle 56, and a mass spectrometer 58 with differential pumping system and an ion transfer interface (not shown in FIGS. 5A-5B). Further, the apparatus 50 includes a quartz capillary 54, which supplies the analyzed sample S. The quartz capillary 54 protrudes through the discharge electrode 51, through the glow discharge chamber 52, and through the sampling conditioning channel 55 and ends in the close vicinity or within the throttle of the sampling nozzle 56. In alternate implementations of the apparatus 50, the tip of the capillary 54 may protrude into the nozzle. To form desired gas flows and a desired gas pressure range of about 3 to 100 mBar in the glow discharge chamber 52, a technically pure (5.0 or 6.0) noble gas (e.g., Argon) is fed to the discharge chamber. The gas is evacuated past the sampling nozzle 56 by a mechanical pump 57, which may operate at a pump speed of 5 L/s or higher. The mechanical pump may be supplied with an oil filter (not shown in FIGS. 5A-5B).

FIG. 5B illustrates a conditioned glow discharge ionization mass spectrometry apparatus 50b similar to the apparatus 50a of FIG. 5A. The apparatus 50b differs from the apparatus 50a in that the apparatus 50b includes an arrangement of the sample conditioning channel 55b formed with an inserted tube 60, unlike the tubeless sample conditioning channel 55a of the apparatus 50a. In operation, a noble gas (e.g., Argon) is fed at a sufficient rate (e.g., between 100-1000 mL/min) to sustain gas pressure between 3 and 100 mbar (e.g., between 10 and 20 mBar), and the nozzle aperture is sized between 0.3 mm and 3 mm (e.g., between 1 mm and 2 mm). An RF or DC voltage in the kilovolt range is connected to electrode 51 via a ballast resistor in the range from 0.3-3.0 MOhm to induce a glow discharge between electrode 51 and a grounded counter-electrode, which is formed either by the walls of the ionization chamber 52, by the reactor chamber 53, or by a conditioning tube 60. The quartz capillary 54 with removed polyimide coating protrudes through the tubular electrode 51 and sampling conditioning channel 55. The capillary 54 may stabilize the glow discharge regime due to surface discharges. The gas flow samples the glow discharge products—including Argon ions $Ar^+$, Argon metastables $Ar^*$, and electrons e—through the reactor chamber 53. Fast electrons charge the insulated quartz capillary, this way inducing a radial electric field that pushes charged particles to walls and leaves metastable atoms within the flow. According to literature, metastable $Ar^*$ atoms live for about 1 second, while transfer time in the interface is between 10-30 ms. The metastable $Ar^*$ excitation energy is 13.6 eV which is enough for Penning ionization of the analyte with any smaller ionization potential expressed as follows.

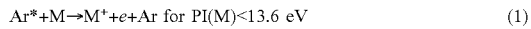

$$Ar^*+M \rightarrow M^++e+Ar \text{ for } PI(M)<13.6 \text{ eV} \qquad (1)$$

In some implementations, Argon metastable atoms are coaxially mixed with analyte molecules in the close vicinity or at the throttle of the sampling nozzle 56. Coaxial mixing preserves a high concentration of the analyte within the gas flow. At 1 mm-2 mm nozzle size and 5-10 L/s pumping speed of the fore-vacuum pump 57, a supersonic jet forms (such a jet forms at the nozzle pressure ratio above 2), which inevitably is a cooling gas jet and provides some cooling of the entrained analyte molecules. As in Cold EI methods, vibrational cooling of this type notably reduces ion fragmentation. Accordingly, gaseous cooling within the supersonic jet improves the softness of the described method of conditioned glow discharge (i.e. a Cold CGD). Cooling is particularly effective, since the entire source has to be at 250-280° C. to avoid sample accumulation at surfaces.

The exemplary apparatus and CGD method differ from the CGD method disclosed in WO 2012/024570 by at least five features and processes: (i) coaxial supply of analyzed sample to concentrate the sample on the flow axis; (ii) stabilizing of glow discharge regime by coaxial quartz capillary protruding through the glow discharge region; (iii) plasma conditioning within a channel in presence of low conductive or insulated (at 250° C.) quartz capillary which promotes removal of charged particles; (iv) minimizing time and number of ion molecular reactions within the reactor by introducing quartz capillary close to the nozzle throttle; and (v) local cooling of analyte molecules at the time of the analyte ionization. Due to the removal of charged species in the conditioner, Penning ionization by metastable Argon atoms becomes the main ionizing channel. In some implementations, Helium is utilized to produce long living metastable atoms for providing a similar ionization mechanism and source analytical parameters with somewhat harsher ionization.

The Cold CGD method of the present disclosure includes the following steps: (a) arranging an enclosed ionization chamber 52 of technically clean materials (stainless steel, ceramics, copper and graphite seals) for minimal outgassing at 250-300 C; (b) heating said ionization chamber 52 to at least 250 C; (c) feeding technically pure (at least 5.0 and preferably 6.0) noble gas into said ionizing chamber 52 at flow rates between 100 to 1000 mL/min; (d) sampling said gas into a nozzle 56 followed by a fore-vacuum pump 57 to arrange a gas flow through the tubular counter-electrode 55 and to sustain gas pressures between 5 and 100 mBar in said ionizing chamber 52; (e) inducing either RF or DC glow discharge at 0.3-10 mA current between tubular electrode 51 and a counter-electrode; (f) stabilizing glow discharge regime by inserting an insulating surface, such as bare quartz capillary 54, through said tubular discharge electrodes 51; (g) sampling discharge products from the discharge region into a counter-electrode by a gas flow through a conductive plasma conditioning channel 55 or 55B with diameter between 1 and 3 mm and length between 5 and 30 mm; (h) protruding bare quartz capillary 54 through said plasma conditioning channel 55 or 55B for removal of charged particles by the electrostatic field of the charged insulating surface; (i) supplying analyzed sample via said quartz capillary at flow rates in the range from 1 to 100 mL/min; (j) sampling glow discharge products and mixing analyzed sample with a conditioned plasma flow in close vicinity or in the throttle of a sampling aperture 56; (k) providing local cooling of the analyte within a supersonic gas jet, formed within and past the aperture 56; (l) sampling reaction products into a mass spectrometer 58, preferably via an intermediate pumping stage in presence of confining radio-frequency fields.

In some implementations the exemplary CGD method is applied for mass spectrometric analysis of complex mixtures of semi-volatile compounds. Components are time separated within a gas chromatograph, ionized in the CGD source, and analyzed in a mass spectrometer. Formation of M+ ions only ease spectra interpretation. The mass spectrometric method may be further improved by inducing fragmentation of M+ ions by injecting said ions into a radio-frequency ion guide at elevated ion energy. Since fragmentation patterns and fragment types are primarily defined by ion structure, fragment spectra appear very similar to fragments in the electron impact ionization. This allows identifying analyte molecules by both molecular mass information and by fitting fragment spectra to NIST library.

The CGD method may provide excellent bases for quantitative information. As described in greater detail below, the ionization efficiency is uniform across wide range of compounds. The signal response remains linear at least within four orders of magnitude, regardless of chemical matrix with up to at least 10 ng/sec flux.

Figure 15:
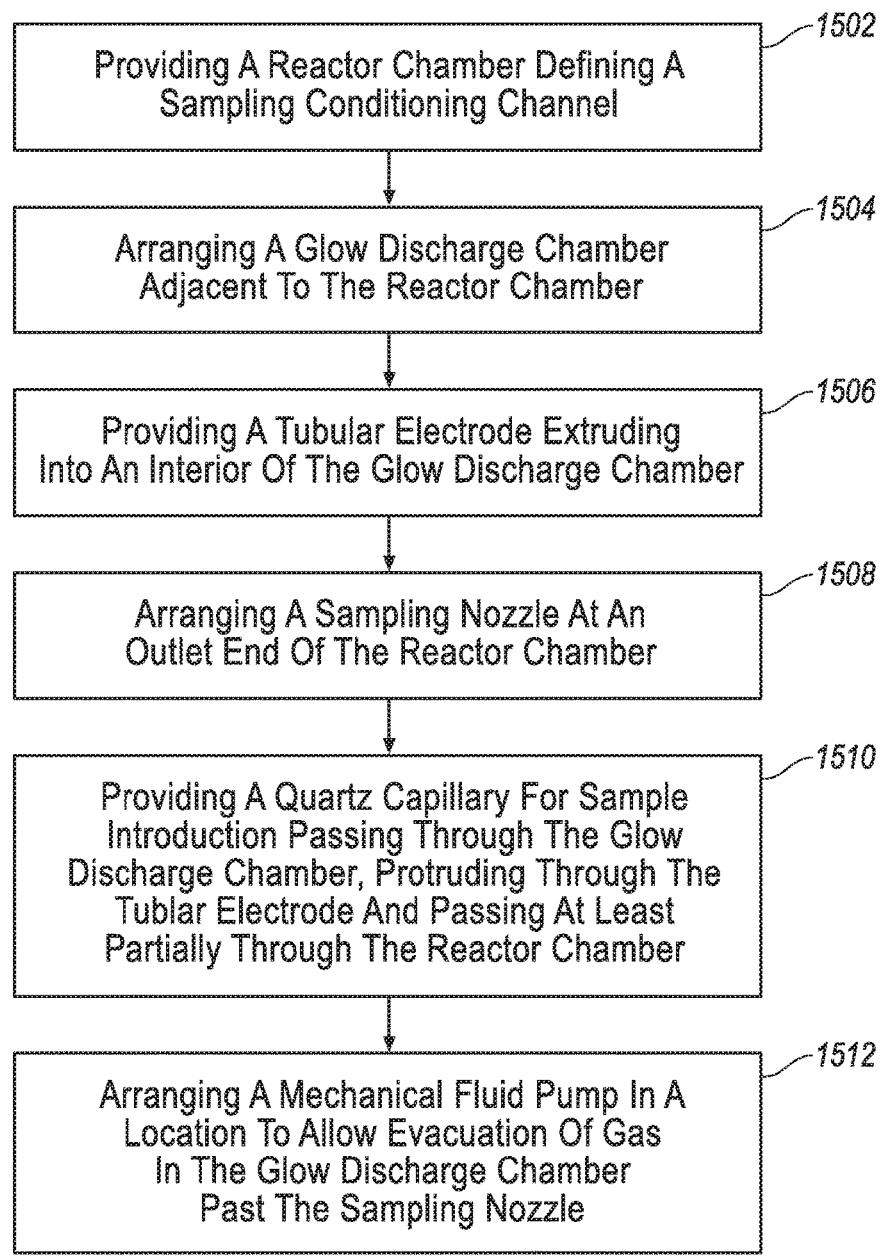
FIG. 15 is a flow chart detailing exemplary operations for making the apparatuses of FIGS. 5A-5B.

Turning to FIG. 15, an exemplary arrangement of operations for a method for assembling a mass spectrometry apparatus is illustrated. At block 1502, the method includes providing a reactor chamber 53 defining a sampling conditioning channel 55. At block 1504, the method includes arranging a glow discharge chamber 52 adjacent to the reactor chamber 53. At block 1506, the method includes providing a tubular electrode 51 extruding into an interior of the glow discharge chamber 52. At block 1508, the method includes arranging a sampling nozzle 56 at an outlet end of the reactor chamber 53. At block 1510, the method includes providing a quartz capillary 54 for sample introduction. The quartz capillary 54 passes through the glow discharge chamber 52, protrudes through the tubular electrode 51, and passes at least partially through the reactor chamber 53. At block 1512, the method includes arranging a mechanical fluid pump 57 in a location to allow evacuation of gas from the glow discharge chamber 52. The evacuation of the gas by the mechanical fluid pump 57 passes the gas by the sampling nozzle 56.

Role of Collisional Cooling in Supersonic Jet

Figure 6A:
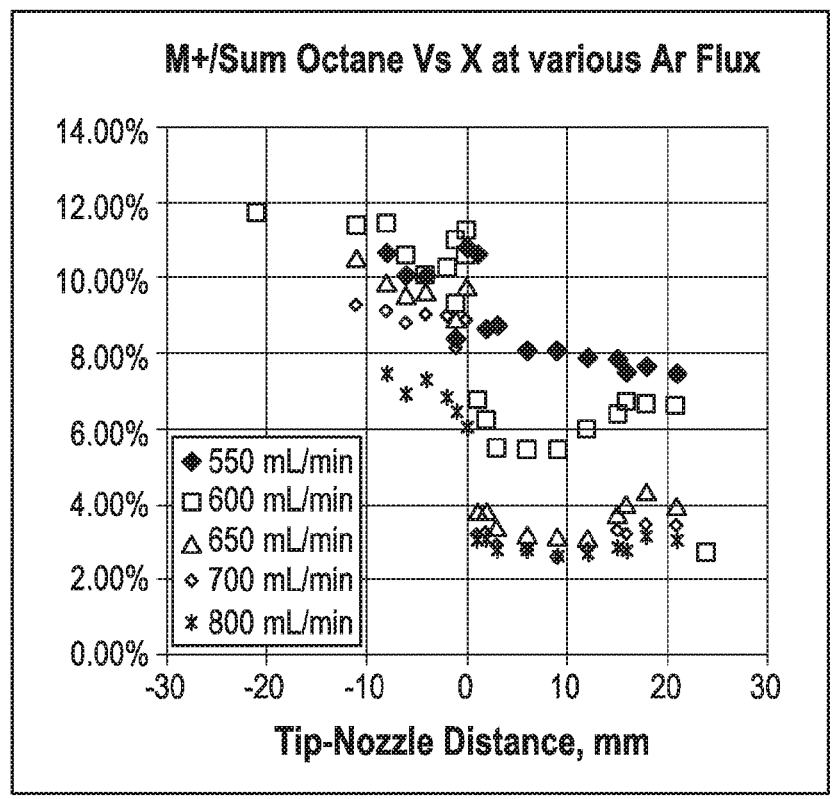
FIGS. 6A-6B show plots relating to effects of a jet used for cooling the CGD method accomplished by the apparatuses of FIGS. 5A-5B.
Figure 6B:
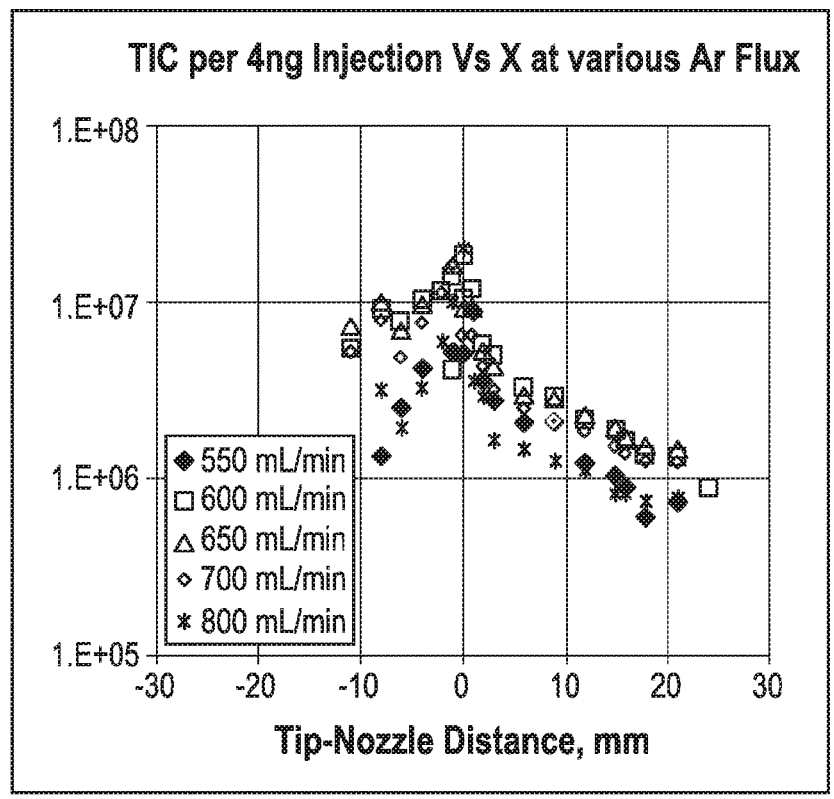

Referring to FIGS. 6A and 6B, softness of the exemplary CGD method is assisted by the analyte cooling in the supersonic jet past the nozzle 56. The plotted representations of FIGS. 6A and 6B present profiles obtained by moving the tip of the capillary 54 relative to the throttle of the supersonic nozzle 56. Measurements have been done at various Argon fluxes into the source at a 1 mm-diameter-sized nozzle 56. The plot of FIG. 6A presents the profile of relative intensity of M+ octane ions versus total Octane spectrum intensity, which reflects the ionization softness. The plot of FIG. 6B presents profiles of signal absolute at 4 ng octane injections. Within the alkane class, small size molecules appear more fragile, and it takes more efforts obtaining strong relative intensity of M+ ion, while higher alkanes are primarily presented by molecular ions. Looking back at softness profiles, the softness improves when capillary reaches the nozzle 56 or protrudes the nozzle 56, and at higher Argon fluxes above 650 mL/min the softness improves 3-4 times (i.e. from 2-3% to 10-12%). Apparently, the maximum total ionic signal is also observed when capillary is placed right into the nozzle throttle. Compared to a 20 mm distance from the nozzle, the signal grows almost 10-fold. The effect may be explained by rapid space-charge expansion of ions formed in the upstream reactor, while ions formed in the nozzle throttle and in the axis of the jet would remain focused and are better transferred within the interface. Thus, the arrangement with coaxial placement of quartz capillary 54 at the nozzle 56 throttle improves both softness and sensitivity of the CGD method.

Identification of Analytes with the Exemplary CGD Method

Figure 7:
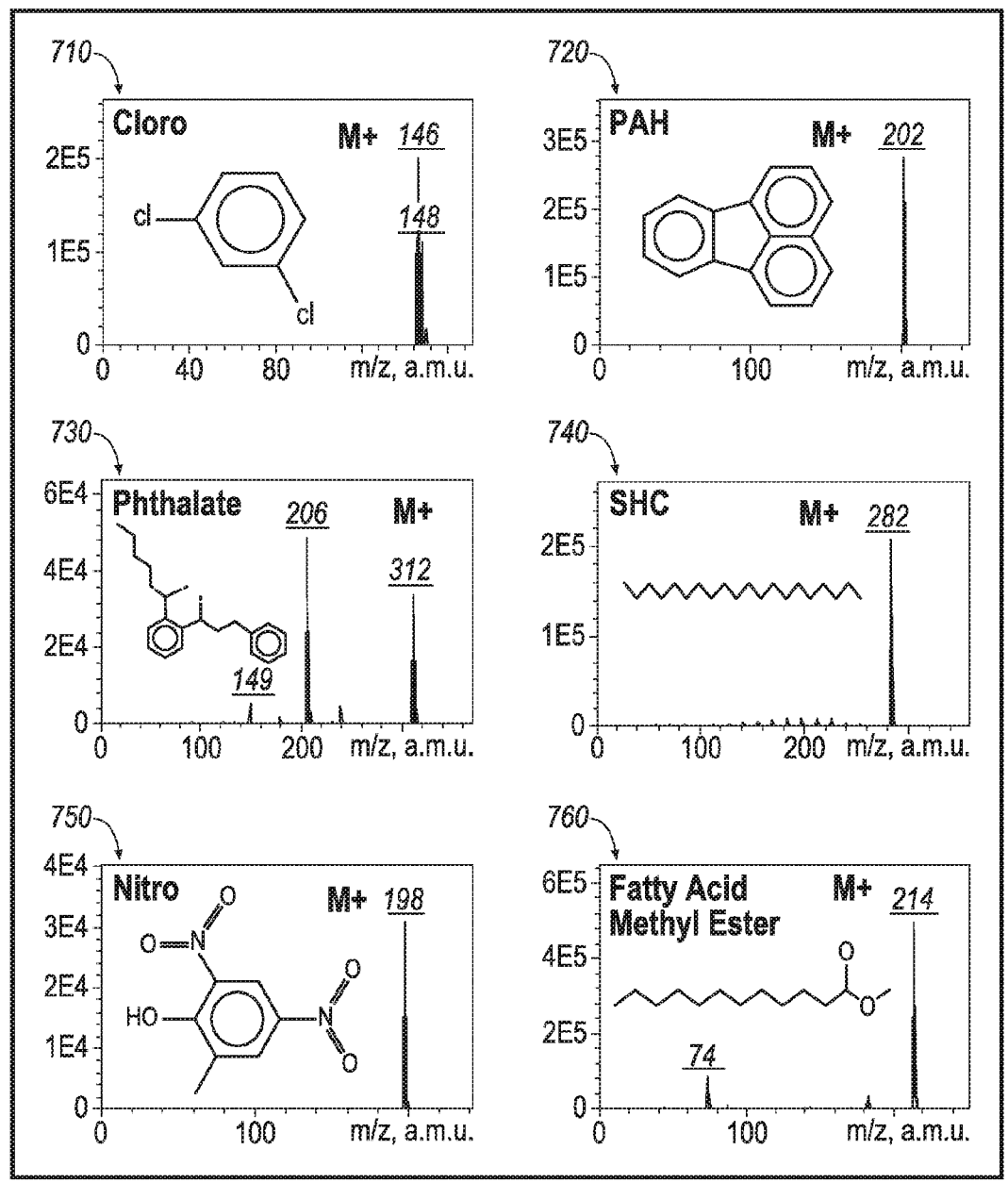
FIG. 7 shows examples of spectra for representative compounds created utilizing the CGD method accomplished by the apparatuses of FIGS. 5A-5B.

Referring to FIG. 7, for a wide range of semi-volatile compounds, the exemplary CGD method forms molecular M+ ions without forming protonated MH+ ions, even for classes with large proton affinities, such as phthalates (see icon 730) and nitroses (see icon 750). This results in simplified spectra interpretation (compared to photo-ionization forming $M-H^+$, $M^+$ and $M+H^+$ ions) and avoids competition for proton, which is known to produce discrimination and matrix effects. In the example shown, the most notable effect is low fragment intensity for larger size alkanes (saturated hydrocarbons SHC, here $C_{20}H_{42}$, see icon 740) and for phthalates. The EI spectra for those compounds produces negligibly small molecular peaks. Known quantitative and semi-quantitative methods, like PI and Cold EI, do not form such intensive molecular peaks for alkanes and also form mixed types of molecular ions. Thus, the disclosed CGD method appears unique in that it forms primarily M+ ions and it is soft (i.e. produces very few fragments).

Figure 8:
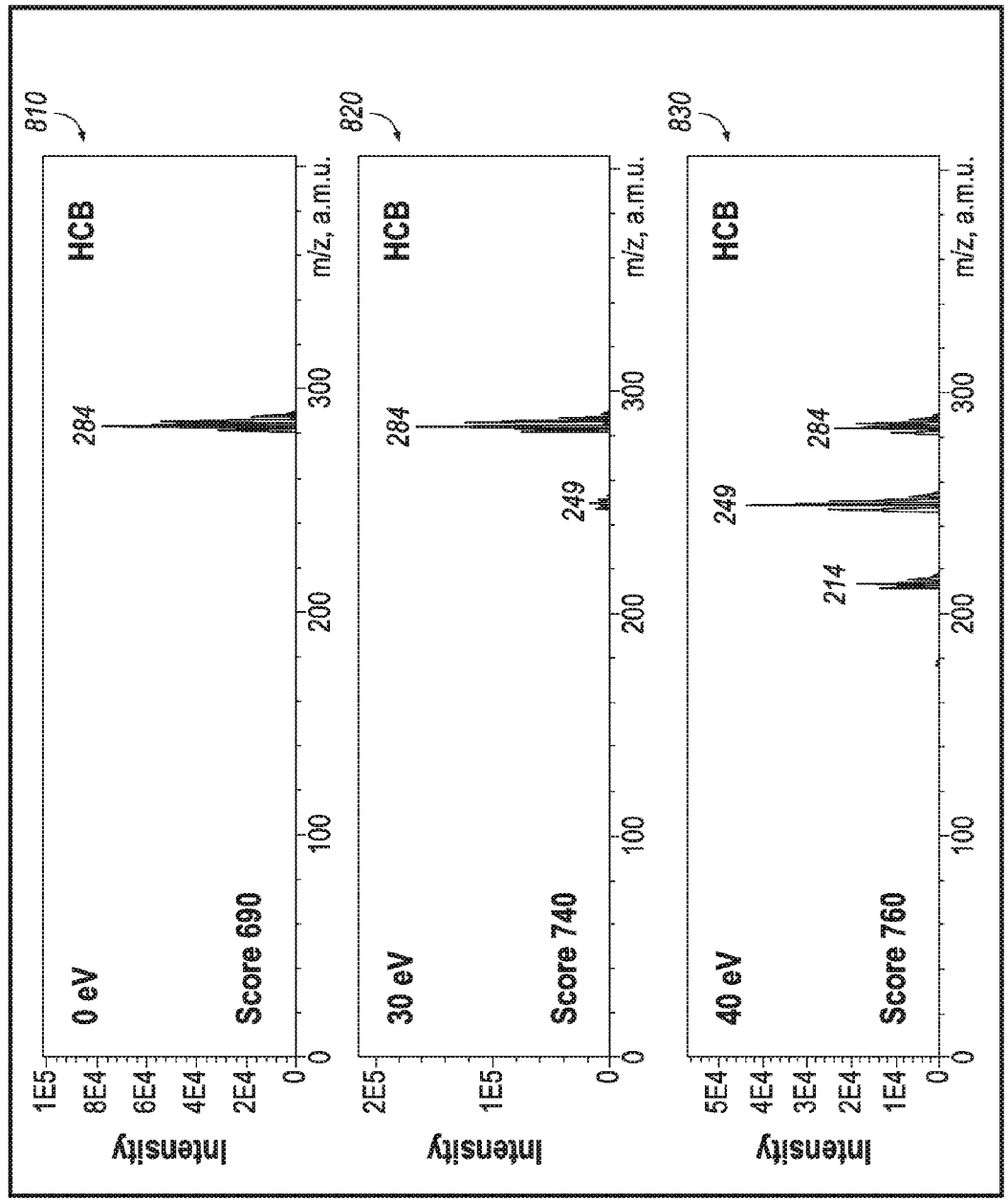
FIG. 8 shows an array of spectra for hexachlorobenzene at various energies of collisional induced dissociation obtained with the CGD method accomplished by the apparatuses of FIGS. 5A-5B.

For the purpose of analyte identification, molecular M+ ions may be fragmented within an ion transfer interface or within a collisional dissociation (CID) cell of a tandem mass spectrometer. Referring to FIG. 8, the exemplary plots 810, 820, 830 show that fragmentation has been induced by increasing ion energy at the entrance of RF ion guide at 10 mTor gas pressure. When ion injection energy has been kept close to zero (plot 810), hexachlorobenzene (HCB $C_6Cl_6$) spectra were presented by molecular ions only. When raising energy to 30 eV (plot 820), minimal amount of fragments M-Cl+ appeared; at 40 eV (plot 830) fragments became more intense than molecular ion. Thus, at CID fragmentation of M+ ions, fragment ions are similar to EI fragments and spectra could be matched with NIST library.

Figure 9:
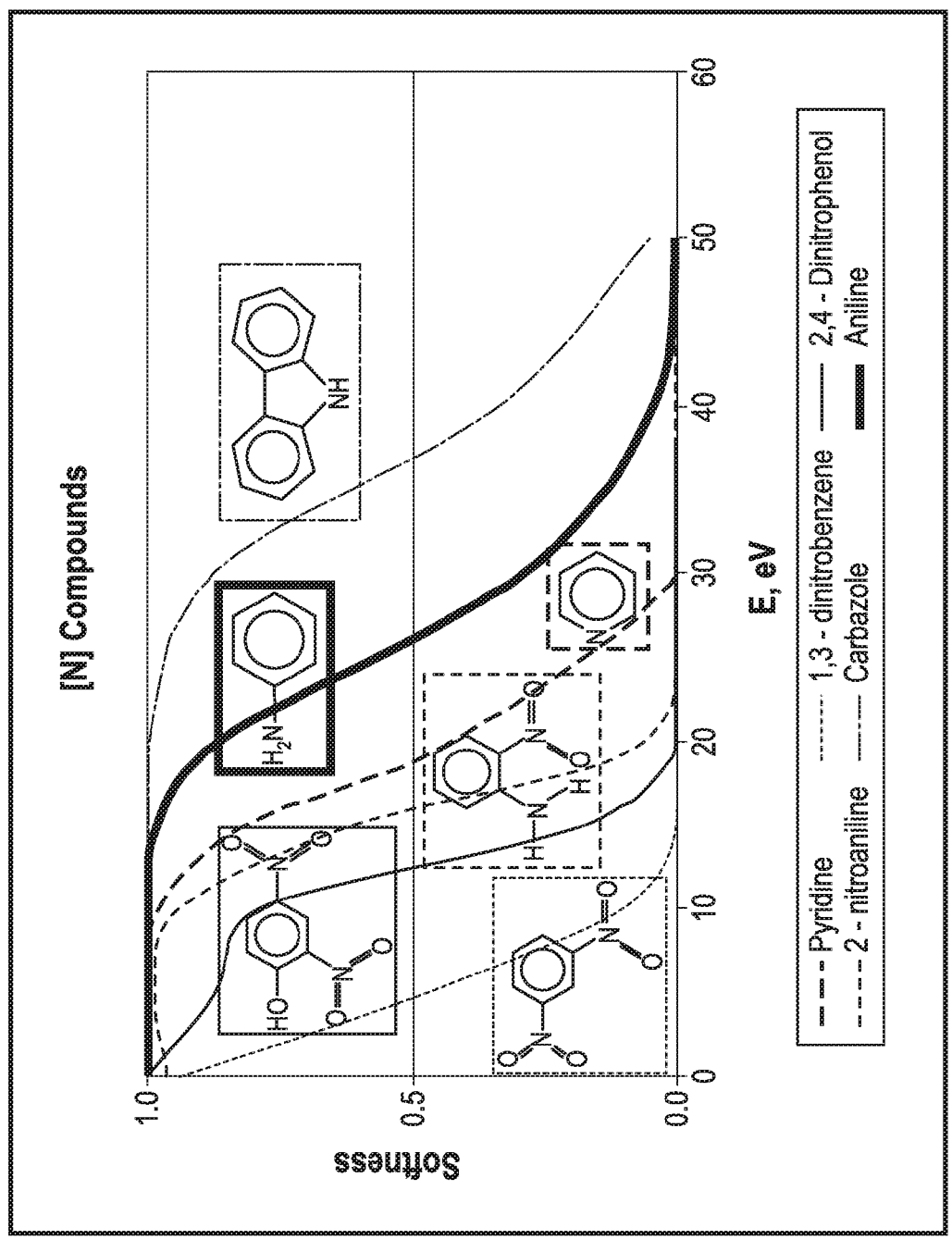
FIG. 9 shows a plot of for survival (relative intensity of molecular M+ ions to the total spectrum intensity) of various types of analyte versus ion injection energy into an RF ion guide incorporated into the apparatuses of FIGS. 5A-5B.
Figure 10A:
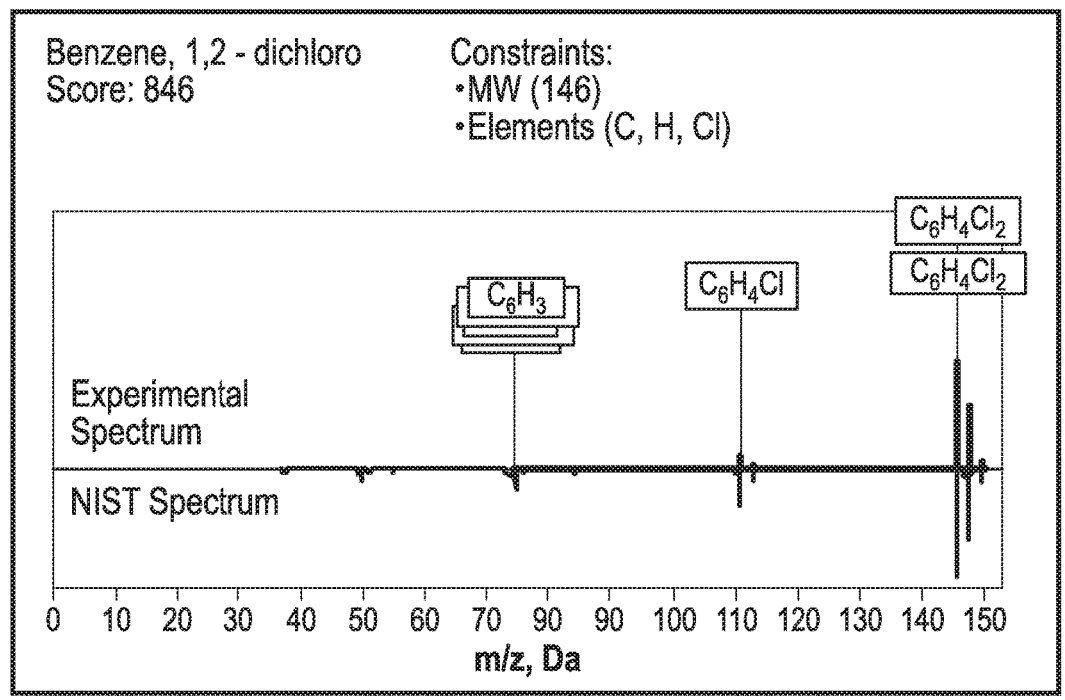
FIGS. 10A-10D show results of a fragment spectra interpretation.
Figure 10B:
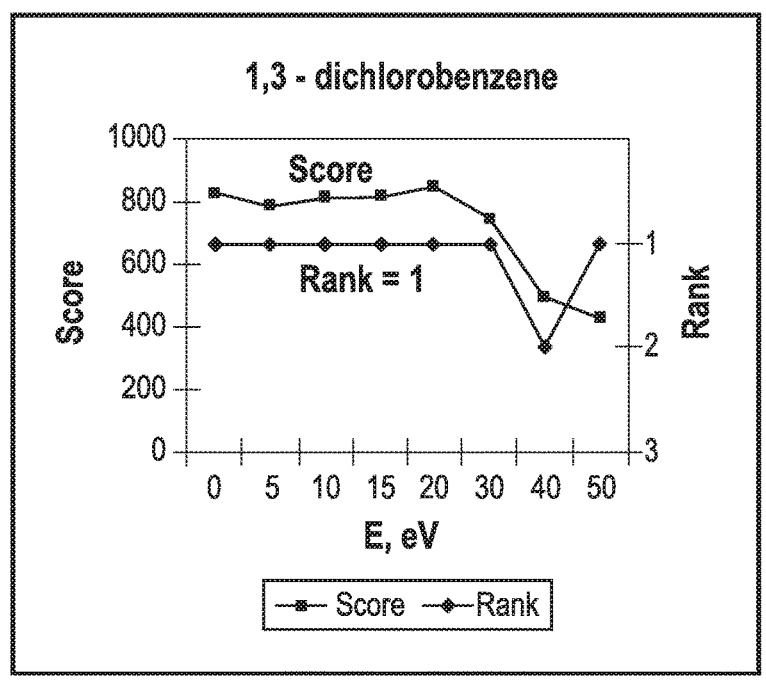
Figure 10C:
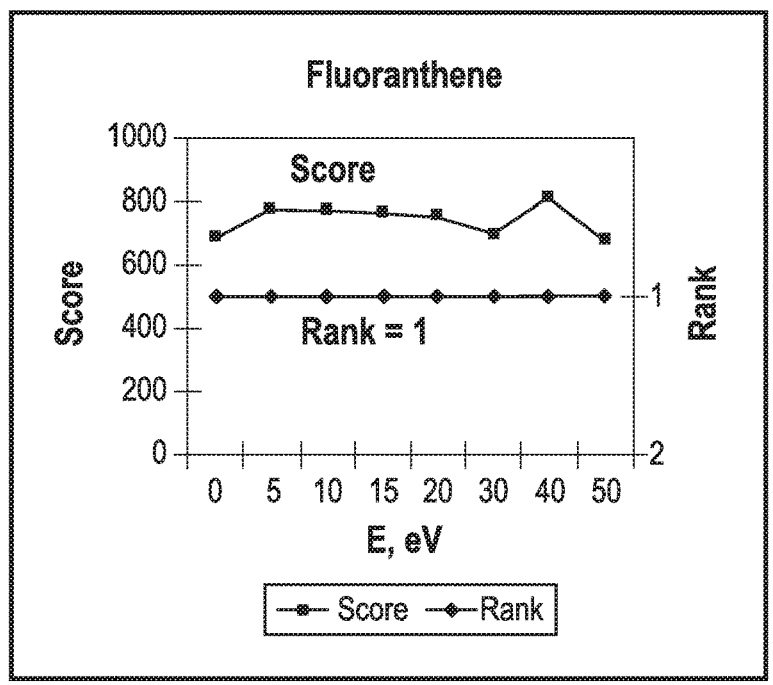
Figure 10D:
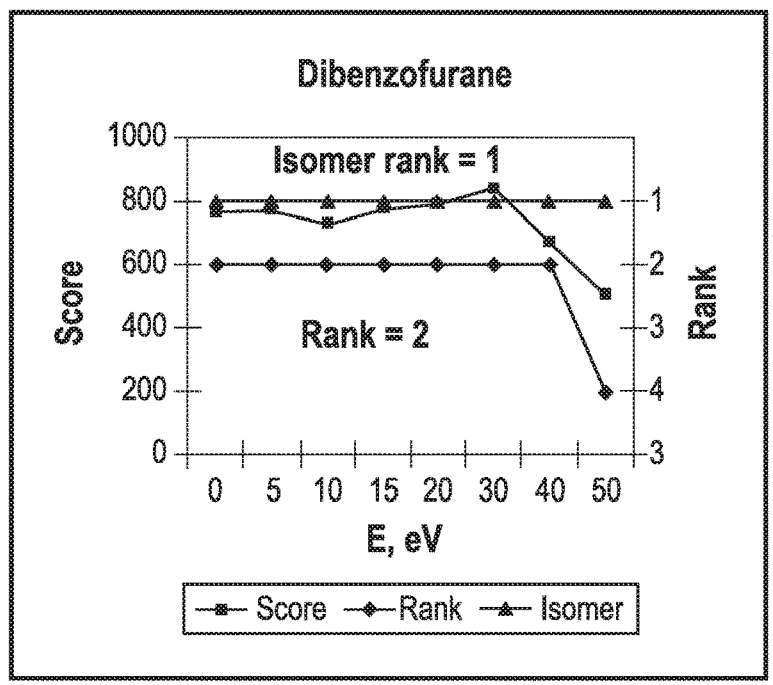

Referring to FIGS. 9-10, optimal fragmentation energy depends on the analyte structure as shown by representative curves for six aromatic compounds on FIG. 9, shows a plot of softness (relative intensity of molecular M+ ions to the total spectrum intensity) versus ion injection energy into RF ion guide. Nevertheless, as shown in FIGS. 10A-10D, standard NIST identification provides high scores around 700-800 over a wide range of fragmentation energies. FIG. 10A compares experimental spectrum of 1,2-dichloro benzene with an NIST spectrum, which is reflected at the bottom part of the plot. The NIST score is 846. Constraining molecular weight and elemental composition (usually automatically derived at high accuracy measurement of molecular weight), the answer appears first in the search list. FIGS. 10B-10D show how the score and the rank depend on the fragmentation energy, E, for three other compounds. For instance, the score remains around 800, and the correct answer has either rank one, or the first answer defines a spatial (not structural) isomer, as in case of dibenzofurane in FIG. 10D. Thus, the disclosed CGD method provides both molecular weight and structural identification within wide range of fragmentation energies and for wide variety of analyte compounds.

Application Example

Figure 11:
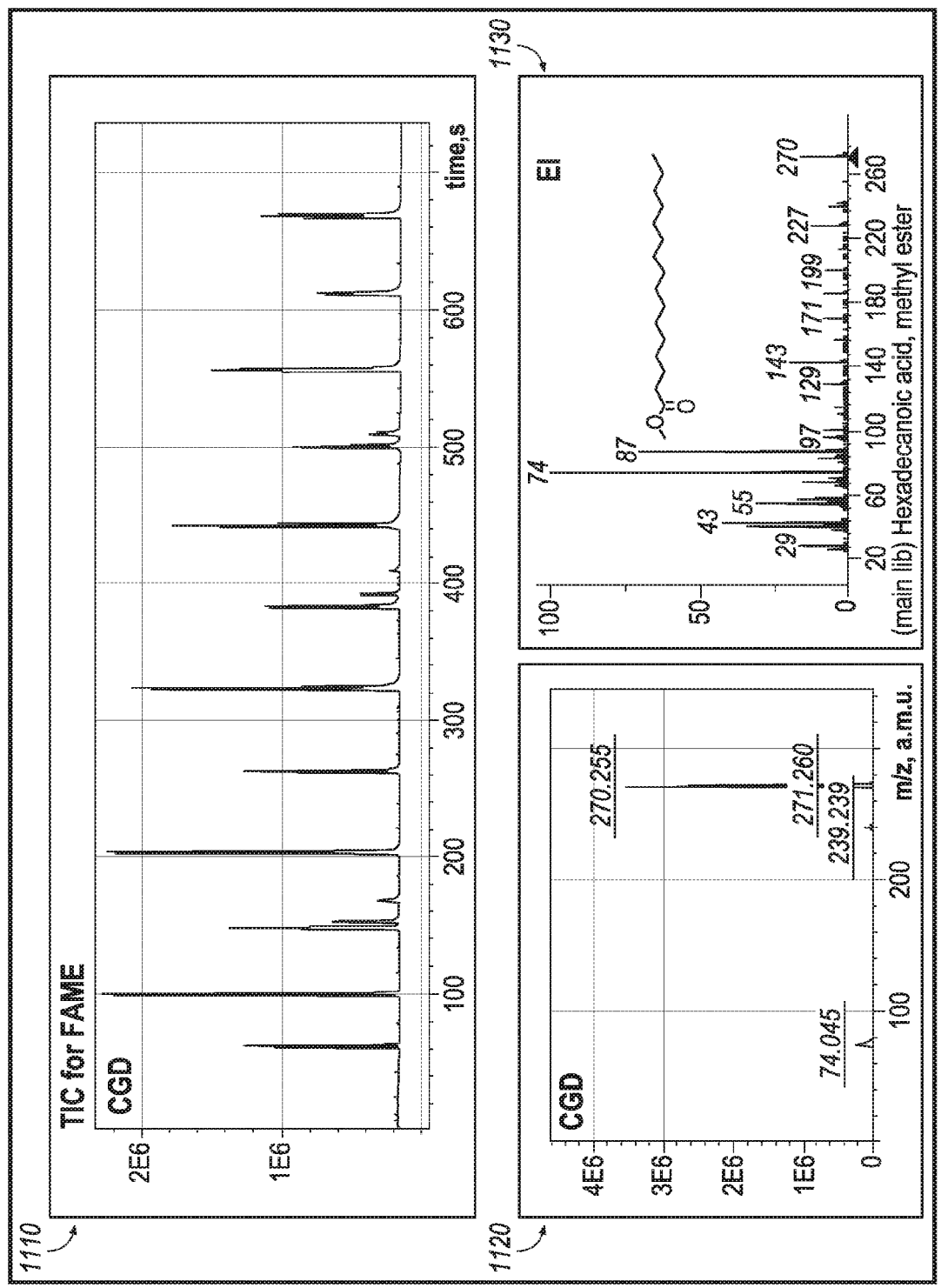
FIG. 11 shows spectra related to analysis of fatty acids methyl esters (FAME).

The CGD source is expected to be particularly useful for petroleomics and metabolomics. Referring to FIG. 11, for an analysis mixture of fatty acids methyl esters (FAME), the CGD method provides a reasonably uniform response between compounds of the same class as seen from total ion current (TIC) trace (plot 1110). The CGD spectra of FAME are presented by M+ ions with about 10% of intensity of all fragments (plot 1120). Fragment ion masses match those in EI (plot 1130).

Quantitative Analysis

Figure 12A:
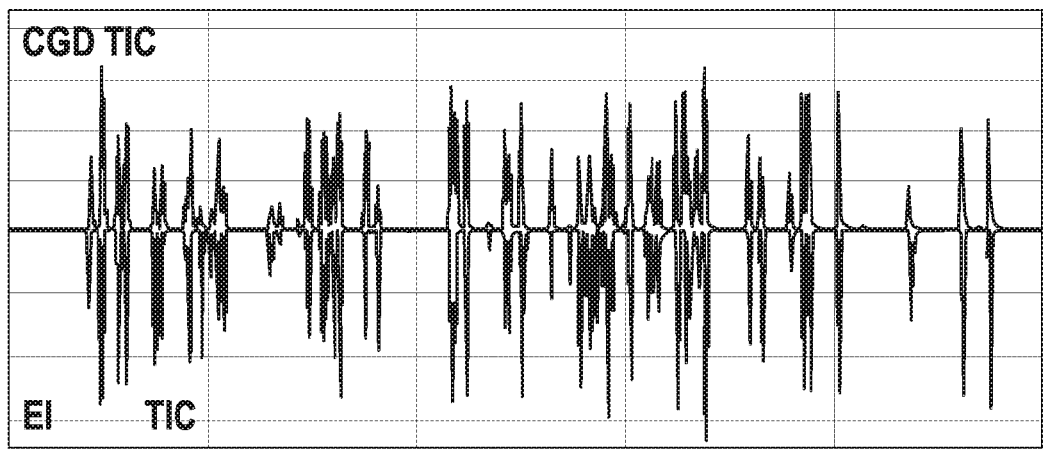
FIGS. 12A-12C show comparisons between a total ion current for CGD and EI methods for a MegaMix sample.
Figure 12B:
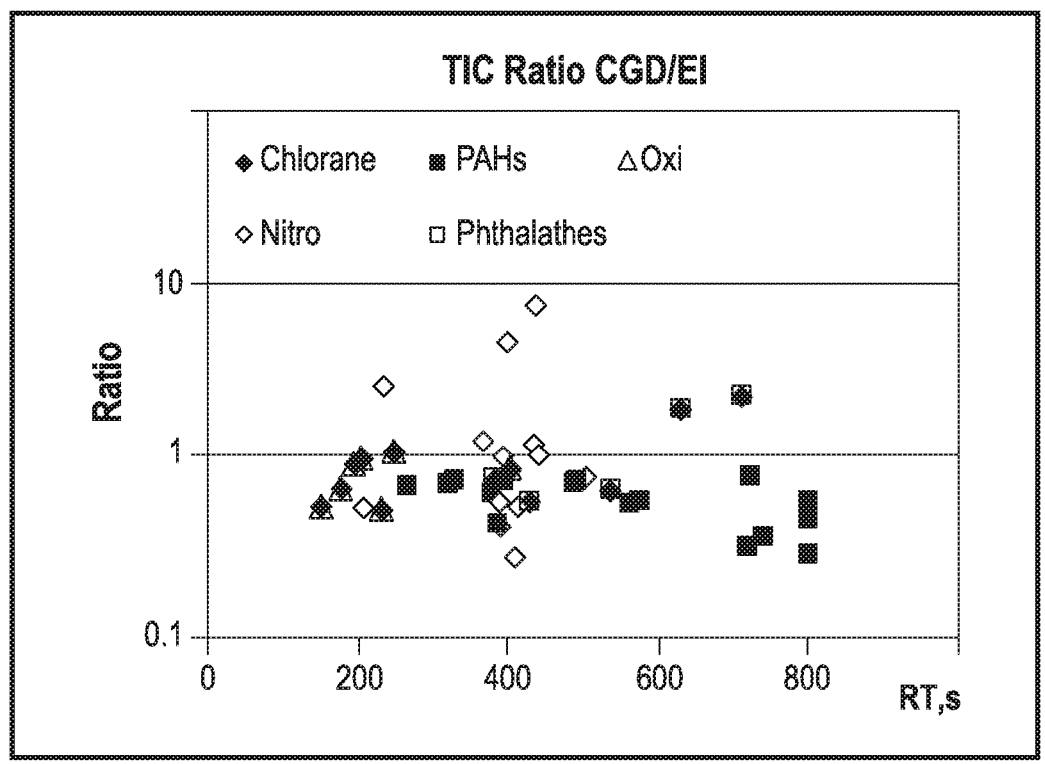
Figure 12C:
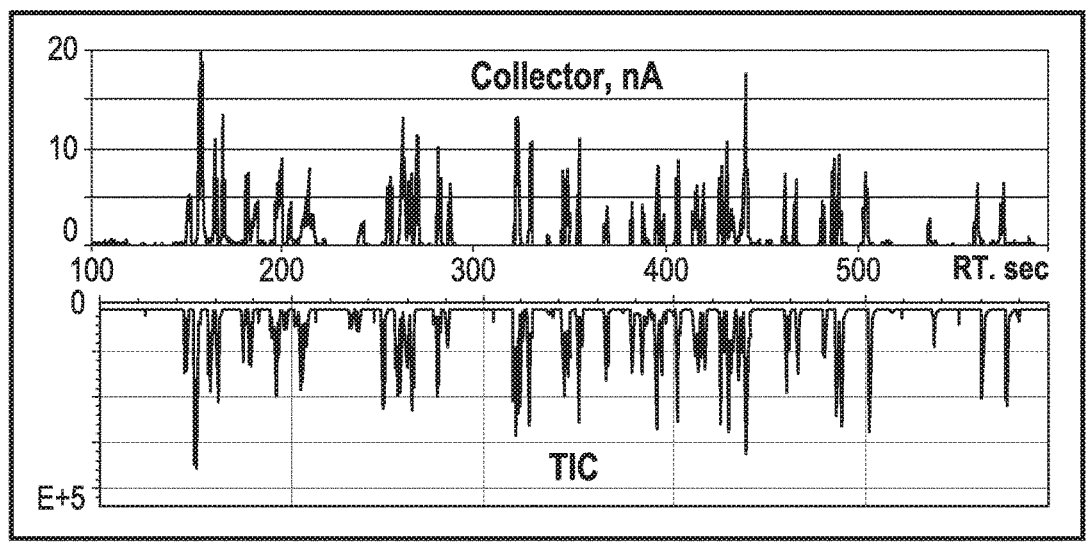

FIGS. 12A-12C compares a total ion current for the CGD and EI methods for a MegaMix sample (Restek) mixture. Since mixtures may degrade at storage, both analyses were made with the same sample at the same day. Signals correlate well between those two methods as seen from TIC comparison of FIG. 12A (CGD method on top and EI reflect below) and from the plot of FIG. 12B (presenting ration of TIC for the CGD and EI methods). Since the EI method is recognized as the golden standard for quantitative analysis, the above correlation indicates uniform ionization efficiency of the exemplary CGD method across wide range of classes, including PAH, PCB, phthalates, nitro and oxy compounds, and for moderate size chlorinated compounds. The correlation presented in FIG. 12C provides additional confirmation. The collector current past CGD source (shown on top) is compared to mass spectrometric signal TIC (shown below). Both correlate well to assure that there no significant discriminations at MS measurements, for example, such as low mass cut off in the RF transfer interface. Overall, FIG. 12C shows that the CGD source ionization efficiency (ratio of produced ions per injected molecules) can be estimated as 1E-3, since 10 ng injections were producing 20 nC charge at the collector. Moderate ionization efficiency is chosen to match the capacity of the transfer interface and the dynamic range of MS detector, while reducing sensitivity to impurities in the source materials and gases.

Figure 13:
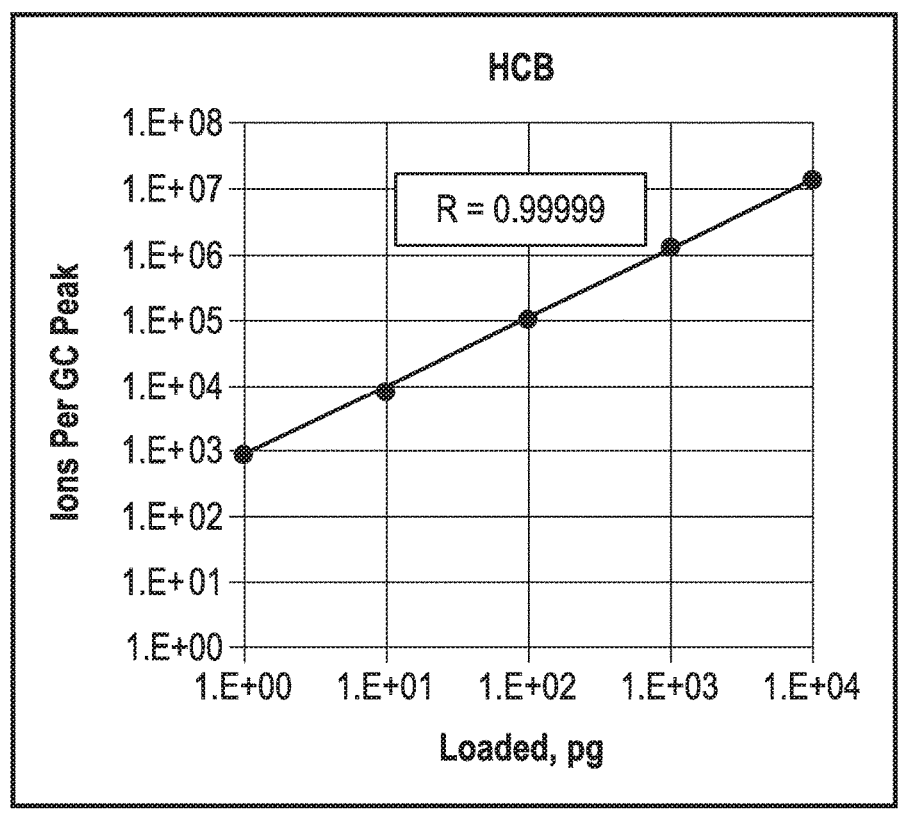
FIG. 13 shows a plot of bi-logarithmic signals versus HCB load onto a gas chromatograph (GC) column illustrating capabilities of CGD for quantitative analysis.

FIG. 13 shows a plot of bi-logarithmic signals versus HCB load onto a gas chromatograph (GC) column illustrating capabilities of CGD for quantitative analysis. In the example shown, the CGD mass spectrometric signal is substantially linear with an amount of injected sample within four orders of magnitude with correlation coefficient R=0.99999. At even higher loads of 100 ng into the GC column, the signal linearity drops by a factor of two, indicating some saturation processes. Measurements of ion currents past the source have indicated that the saturation at high loads is more likely to occur within the ion transfer interface, e.g., by space charge effects within an RF quadruple at ion currents above 20 nA (see FIG. 12C).

Analytical Summary

Overall, the exemplary CGD method provides a unique combination of analytical properties: (a) the method is soft for wide range of tested semi-volatile compounds, including the compounds which form negligible molecular peak in the EI method; (b) the CGD method forms primarily molecular ions, which ease spectra identification, since there are no other types of quasi-molecular ions; (c) optionally induced CID fragmentation allows NIST identification with high confidence, particularly when applying constrain on the molecular mass, known from measurements without the controllable fragmentation; (d) ionization efficiency is fairly uniform across wide range of chemical classes, which is very attractive at quantitative analysis, particularly when standards are not available; (e) the ionization efficiency stays constant and the signal remains linearly proportional to concentration in at least four orders of dynamic range. The latter two properties provide good bases to absence of matrix discrimination and mutual interference effects at sample fluxes under 10 ng/sec.

The novel features of the disclosed CGD method allow a novel generic analytical method to be formulated. The novel generic analytical method includes the following steps: (a) quantitative and soft ionization in a conditioned glow discharge ion source; (b) alternated in time measurement of molecular mass and fragmentation of molecular ions; and (c) compound identification by comparing with a library of electron impact spectra.

Range of Volatility

Analyte volatility for the disclosed CGD method is range-limited simply due to the method's coupling to a gas chromatograph, where most non-volatile compounds would not pass without chemical modifications. However, based on the above measurements of the upper load being 10 ng/sec, the disclosed CGD method may retain its analytical merits at moderate load levels of solvents or matrix up to 10 ng/sec. Thus, the disclosed CGD method is compatible with additional methods of sample injection, such as: (a) direct thermal desorption; (b) desorption by laser; (c) sample nebulization with sampling of aerosol via curtain gas (preventing sampling of the vast majority of the solvent); and (d) liquid spray at liquid fluxes under 10 nL/min from either CE or nano-LC.

Formulation of the CGD Method

While analyzing multiple processes occurring in the CGD source novel features responsible for analytical merits include: (a) conditioning of the glow discharge at fore-vacuum gas pressure achieved by sampling glow discharge products in the gas flow and passing them through a coaxial channel with insulating capillary on axis, providing effective removal of charged particles, while effectively transferring metastable atoms of noble gases; and (b) injecting a sample into a flow of metastable atoms in close vicinity of the throttle of the supersonic nozzle. The process of injecting the sample (b) causes several positive effects: (i) effective focusing of the analyte on the jet axis and ensures an effective ion transfer in the subsequent transfer interface; avoids contact of analyte with the source walls; and (ii) provides vibrational cooling of the analyte, which in turn assists better softness of the ionization method.

Figure 16:
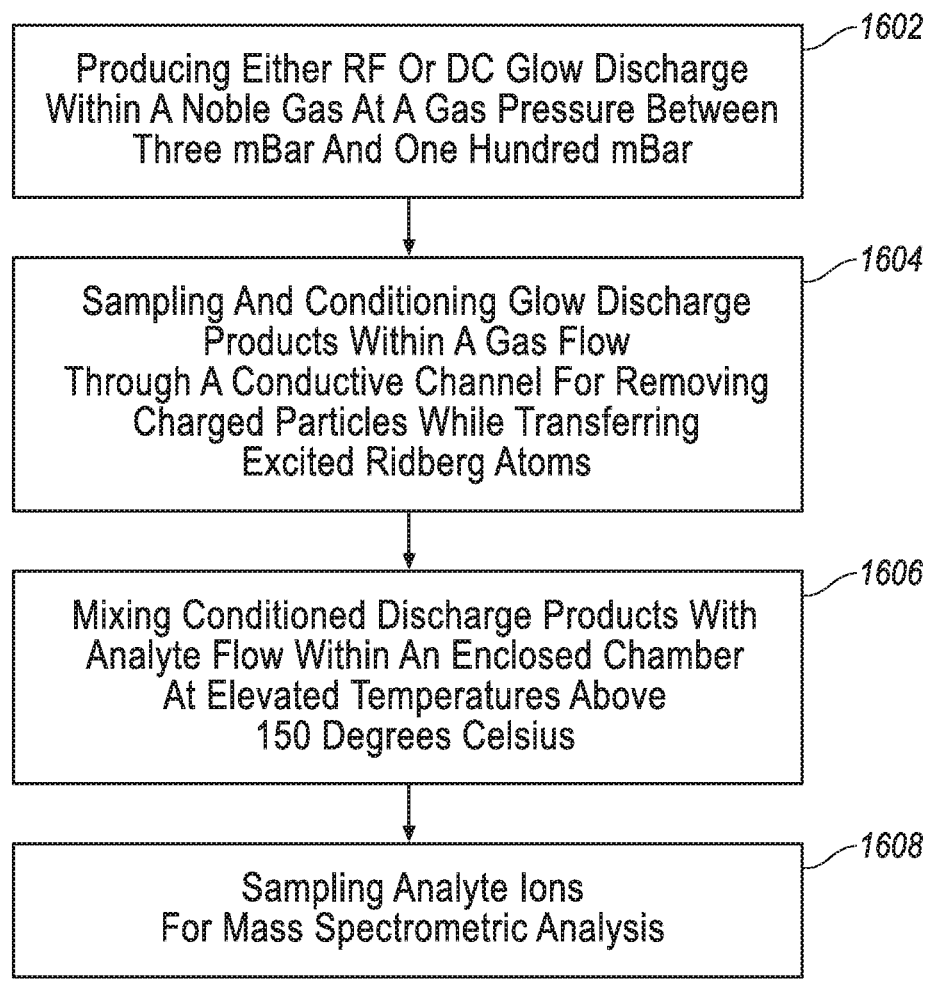
FIG. 16 is a flow chart detailing exemplary operations for performing mass spectrometric analysis including the CGD method accomplished by the apparatuses of FIGS. 5A-5B.

Turning to FIG. 16, an exemplary arrangement of operations for a method of mass spectrometric analysis undertaken by the conditioned glow discharge ionization mass spectrometry apparatus 50 is illustrated. At block 1602, the method includes producing either RF or DC glow discharge within a noble gas at a gas pressure between 3-100 mBar. The glow discharge is produced in a glow discharge chamber 52 between a coaxial discharge tubular electrode 51 and a counter-electrode. The noble gas may be implemented as a variety of noble gases, such as Helium, Argon, or Krypton. At block 1604, the method includes sampling and conditioning the glow discharge products within a gas flow while transferring excited Ridberg atoms. The gas flow is driven by a mechanical fluid pump 57. The glow discharge products are sampled and conditioned through a conductive channel 55. At block 1606, the method includes mixing the conditioned discharge products with analyte at elevated temperatures (i.e. above 150° C.) to produce a Penning reaction between analyte molecules and the Ridberg atoms. This mixing occurs in an enclosed chamber and generates ions of the analyte. At block 1608, the method includes sampling the analyte ions for mass spectrometric analysis in the mass spectrometer 58. A gas flow samples the into the mass spectrometer 58. Generally, the method may be improved with one of the following additional steps: (a) removing charge within the sampling conditioning channel 55 by charging of an insulating surface protruding through the sampling conditioning channel 55; (b) coaxially mixing the analyte flow with the flow of conditioned plasma; or (c) cooling the mixed flow within a sonic or supersonic jet for reducing the region of Penning ionization to cold jet.

Enhanced Peak Capacity

As a further extension of analytical utility, the CGD source has very rapid reaction time. The flow is arranged without pockets and the source walls avoid lengthy analyte absorption. Yet, there is no additional peak tailing, and the source is compatible to fast GC×GC separation, similar to the glow discharge source of WO 2012/024570 (CGD), which is fully incorporated herein by reference. The combined power of (a) GC×GC separation with typical 10,000 peaks capacity and (b) soft and quantitative ionization in the CGD source, would particularly shine for a high resolution multi-reflecting TOF mass spectrometer (MRTOF-MS). Preferably, the high resolution MRTOF-MS employs a collisional dampening interface and a double orthogonal accelerator, operating in the regime of frequent encoded pulsing (EFP) as described in WO 2005/001878 (MRTOF), WO 2007/044696 (OA), and WO 2011/135477 (EFP), each of which is fully incorporated herein by the reference. Such combination is expected to have an overall peak capacity over 10 million, though not accounting for redundancy between chromatographic and accurate mass separation techniques.

As already described, the CGD source is at least compatible with GC and CE upfront separations, both by the speed and by the flux of matrix and carrier fluids. Thus, the advantage of high peak capacity is expected also in cases of using such chromatographic tandems as: (i) GC×GC; (ii) LC-GC; (iii) LC-LC; (iv) LC-CE.

Enhanced Selectivity

As another extension of analytical utility, selectively is enhanced when utilizing the disclosed CGD method. Simply, users want to see target compounds at maximal selectivity, reliability, and sensitivity, while they do not want additional information on the rich matrix and accompanying analyte components. Target analysis with CGD ion source could be enhanced in multiple ways. First, selectivity of ionizing some particular analyte classes may be enhanced by adding a reagent gas into the volume of conditioned plasma. In one example, acetone reagent would promote the soft ionization of polar molecules. Additional small flow may be added, for example, into the carrier Helium gas of gas chromatograph or into the source reagent zone via separate line. Second, molecular ions could be mass selected by either a mass filter (such as quadrupole mass filter) or in a mobility separator. Third, the selectivity and separation capacity of the method could be enhanced by an ion mobility separation. A complimentary analytical power occurs when such separation methods are combined with quantitative and soft ionization. Finally, both separation power and analysis selectivity of CGD mass spectrometric analysis may be enhanced if alternating or scanning the fragmentation energy.

What is claimed is:

1. A method of mass spectrometric analysis, the method comprising the following steps:
    producing either RF or DC glow discharge within a noble gas at gas pressure between 3 and 100 mBar;
    sampling and conditioning glow discharge products within a gas flow through a conductive channel for removing charged particles while transferring excited Rydberg atoms;
    mixing conditioned discharge products with analyte flow within an enclosed chamber at elevated temperatures above 150° Celsius for producing Penning reaction between analyte molecules and said Rydberg atoms to generate ions of said analyte;
    sampling by a gas flow said analyte ions for mass spectrometric analysis;
    providing a tubular electrode extending into an interior of a glow discharge chamber;
    providing a capillary for sample introduction, wherein the capillary passes through the glow discharge chamber, protrudes through the tubular electrode, and at least partially passes through the enclosed chamber; and
    at least one of the following steps:
        (i) removing charge within said conductive channel caused by charging of an insulating surface protruding through said conductive channel;
        (ii) coaxially mixing of analyte flow with the flow of conditioned plasma to form a mixed flow; or
        (iii) cooling of said mixed flow within a sonic or supersonic jet for reducing a region of Penning ionization of the analyte molecules.

2. The method of claim 1, wherein said ions of analyte are partially fragmented either at an ionization event or at a step of controllable collisional induced dissociation, wherein obtained fragment spectra are compared with library spectra of electron impact for analyte identification and for a structure elucidation.

3. The method of claim 2, further comprising introducing less volatile compounds within a liquid or solid matrix to extend the range of analyte volatility whereat a matrix flux remains under 10 ng/sec and where the analyte sample is brought to a gas phase by one of the following steps:
    (a) applying a rapid thermo desorption;
    (b) applying pulsed laser desorption;
    (c) applying nebulization of a liquid sample with removal of solvent vapors by side or counter gas while passing through aerosol; and
    (d) applying nebulization at a flow rate under 10 nL/min past capillary electrophoresis or nano liquid chromatography.

4. A method as in claim 1, further comprising a step of upstream tandem chromatographic separation of the list comprising: (i) GC×GC; (ii) LC-GC; (iii) LC-LC; (iv) LC-CE.

5. A method as in claim 2, for the purpose of enhanced selectivity at analysis of complex mixtures, further comprising a step of mass or ion mobility selection of parent ions prior to the step of ion fragmentation.

6. A method as in claim 2, further comprising a step of varying fragmentation energy.

7. A method as in one of claims 1 to 6, for the purpose of enhanced analysis selectivity, further comprising a step of adding a reagent gas into the conductive channel, thus converting Rydberg ions into reagent ions.

8. A method as in claim 1, further comprising a step of mass-spectrometric analysis of ionized analyte ions with a high resolution multi-reflecting time-of-flight mass spectrometer.

9. A method for assembling an ion source for a mass spectrometry apparatus, comprising:
    providing a reactor chamber defining a sampling conditioning channel;
    arranging a glow discharge chamber adjacent to the reactor chamber;
    providing a tubular electrode extruding into an interior of the glow discharge chamber;
    arranging a sampling nozzle at an outlet end of the reactor chamber;
    providing a capillary for sample introduction, wherein the capillary passes through the glow discharge chamber, protrudes through the tubular electrode, and at least partially passes through the reactor chamber; and
    arranging a mechanical fluid pump in a location to allow evacuation of gas, wherein the mechanical fluid pump evacuates the gas from the glow discharge chamber past the sampling nozzle.

10. The method of claim 9, further comprising:
    charging an insulated surface that protrudes through the sampling conditioning channel.

11. The method of claim 9, wherein the gas evacuated by the mechanical fluid pump comprises a noble gas, and wherein the noble gas is pressurized within the glow discharge chamber prior to evacuation.

12. An ion source for a mass spectrometry apparatus, comprising:

reactor chamber defining a sampling conditioning channel;

a glow discharge chamber residing adjacent to the reactor chamber;

a tubular electrode extruding into an interior of the glow discharge chamber, wherein the tubular electrode receives a voltage;

a sample nozzle residing at an outlet end of the reactor chamber;

a capillary for sample introduction, wherein the capillary passes through the glow discharge chamber, protrudes through the tubular electrode, and at least partially passes through the reactor chamber; and a mechanical fluid pump residing in a location to allow evacuation of gas, wherein the mechanical fluid pump evacuates the gas from the glow discharge chamber past the sampling nozzle.

13. The ion source of claim 12, further comprising:

an insulated surface that protrudes through the sampling conditioning channel.

14. The ion source of claim 12, wherein the gas evacuated by the mechanical fluid pump comprises a noble gas, and wherein the noble gas is pressurized within the glow discharge chamber prior to evacuation.

15. A method of conditioned glow discharge ionization, comprising:

arranging an enclosed ionization chamber for minimal outgassing;

heating the ionization chamber to an elevated temperature above 250 degrees Celsius;

feeding a noble gas into the ionization chamber at a flow rate between one hundred milliliters per minute and one thousand milliliters per minute;

evacuating the gas through a sampling conditioning channel;

inducing glow discharge between a tubular electrode and a counter-electrode, the tubular electrode extending into an interior of the ionization chamber;

inserting a capillary for sample introduction, the capillary having an insulating surface extending through the tubular electrode to stabilize the glow discharge inducement;

creating a gas flow through the sampling conditioning channel to move the induced glow discharge products;

protruding the insulating surface through the sampling conditioning channel;

wherein the capillary passes through the ionization chamber and at least partially passes through the sampling conditioning channel;

introducing an analyte sample;

mixing the analyte sample with the glow discharge products in close vicinity or within a throttle of a sampling aperture;

providing local cooling of the analyte sample within a gas cooling jet, wherein the gas cooling jet is formed within or around the sampling aperture; and directing products to a mass spectrometer.

16. The method of claim 15, wherein the capillary is a quartz capillary, and wherein the quartz capillary introduces the analyte sample.

* * * * *